United States Patent
Novick et al.

(10) Patent No.: US 6,458,932 B1
(45) Date of Patent: Oct. 1, 2002

(54) INTERFERON-α/β BINDING PROTEIN, ITS PREPARATION AND USE

(75) Inventors: Daniela Novick, Rehovot; Batya Cohen, Tel-Aviv; Menachem Rubinstein, Givat Shmuel, all of (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 08/472,402

(22) Filed: Jun. 7, 1995

Related U.S. Application Data

(60) Division of application No. 08/385,191, filed on Feb. 7, 1995, now Pat. No. 5,821,078, which is a continuation-in-part of application No. 08/115,741, filed on Sep. 3, 1993, now abandoned.

(30) Foreign Application Priority Data

| | | |
|---|---|---|
| Sep. 3, 1992 | (IL) | 103052 |
| Aug. 4, 1993 | (IL) | 106591 |
| Feb. 7, 1994 | (IL) | 108584 |

(51) Int. Cl.[7] ............... C07K 14/715; C07K 14/555; A61K 39/395; C07M 21/04
(52) U.S. Cl. ............. 530/351; 530/387.9; 530/387.1; 530/389.1; 530/388.1; 530/300; 435/69.1; 514/2
(58) Field of Search ............ 435/69.1; 530/350, 530/387.1, 388.1, 389.1, 351, 387.9; 514/2

(56) References Cited

U.S. PATENT DOCUMENTS 5,516,515 A * 5/1996 Vellucci ............ 424/184.1

FOREIGN PATENT DOCUMENTS

| | | |
|---|---|---|
| EP | 0369877 | 5/1990 |
| EP | 0588177 | 3/1994 |
| FR | 2657881 | 8/1991 |
| WO | 91/05862 | 5/1991 |
| WO | 92/18626 | 10/1992 |

OTHER PUBLICATIONS

Colwell et al., Methods in Enzymology, 121, 42–51, 1986.*
Eid et al., Biochimica et Biophysica Acta, 1034, 114–117, 1990.*
Lutfalla et al., Embo J., 14, 5100–5108, 1995.*
Novick et al., Cell, 77, 391–400, 1994.*
George et al., Macromolecular Sequencing and Synthesis Selected Methods and Applications, 127–149, 1988, Alan R. Liss, Inc.*
Novick, Daniela et al, "The Human Interferon alpha/beta Receptor: Characterization and Molecular Cloning", Cell, vol. 77, pp. 391–400 (May 6, 1994).
Lutfalla, et al, Embo J., vol. 14, pp. 5100–5108 (1995).
Domanski et al, J. Biol. Chem., vol. 270, pp. 21606–21611 (1995).
Novick et al., Purification of soluble cytokine receptors form normal human urine by ligand–affinity and immunoaffinity chromatography, Journal Of Chromatography, vol. 510, pp. 331–337, Jun. 27, 1990.
Lutfalla et al., The Structure of the Human Interferon α/β Receptor Gene, The Journal of Biological Chemistry, vol. 267, No. 4, pp. 2802–2809, Feb. 5, 1992.
Novick et al., Soluble interferon–α receptor molecules are present in body fluids, FEBS Letters, vol. 314, No. 3, pp. 445–448, Dec. 1992.
Branca et al, Evidence that Types I and II Interferons have Different Receptors, Nature, vol. 294, pp. 768–770, Dec. 1981.
Uze et al., Genetic Transfer of a Functional Human Interferon α Receptor into Mouse Cells: Cloning and Expression of its cDNA, Cell, vol. 60, pp. 225–234, Jan. 26, 1990.
Colamonici et al, Characterization of Three Monoclonal Antibodies that Recognize the Interferon α 2 Receptor, Proc. Natl. Acad. Sci. USA, vol. 87, pp. 7230–7234, Sep. 1990.
Stewart et al., Induction of Type 1 Deabetes by Interferon–α in Transgenic Mice, Science, vol. 260, pp. 1942–1946, Jun. 25, 1993.
Klippel et al., Serum Alpha Interferon and Lymphocyte Inclusions in Systemic Lupus Erythematosus, Annals of the Rheumatic Diseases, vol. 44, pp. 104–108, 1985.
Novick et al., J. Exp. Med., vol. 170, p. 1409, 1989.

* cited by examiner

Primary Examiner—Yvonne Eyler
Assistant Examiner—Nirmal S. Basi
(74) Attorney, Agent, or Firm—Browdy and Neimark

(57) ABSTRACT

Interferon α/β binding proteins are provided, which are capable of modulating the activity of interferon-α subtypes as well as interferon-β. Cloning of DNA molecules encoding these proteins, expression in host cells and antibodies against the proteins are also provided.

19 Claims, 11 Drawing Sheets

FIG. 1A

|BamHI
5' TACTGGATCCATGGTNAARTTYCCNWSNAYHGT →
1 .........MetValLysPheProSerIleValGluGluGluLeuGlnPheAspLeuSerLeuValIleGluGluGlnSerGluGlyIle...27
                                                    ←TAHCTYCTYGTYWSNCTYCCNTACAGCTGAACT 5'
                                                                                        |SalI
(N= A,T,G,C; R= A,G; Y= C,T; W= A,T; S= G,C; H= A,C,T; D= A,G,T)

5' GAG GAA GAA TTA CAG TTT GAT TTA TCT CTC GTC AT  3'
3' Glu Glu Glu Leu Gln Phe Asp Leu Ser Leu Val Ile 20

FIG. 2

```
ATGCTTTTGAGCCAGAATGCCTTCATCTTCAGATCACATAATTTGGTTCTCATGGTGTAT    60
 M  L  L  S  Q  N  A  F  I  F  R  S  H  N  L  V  L  M  V  Y  -  20
 s

ATCAGCCTCGTGTTTGGTATTTCATATGATTCGCCTGATTACACAGATGAATCTTGCACT   120
 I  S  L  V  F  G  I  S  Y  D  S  P  D  Y  T  D  E  S  C  T  -  40
          n1→     n2→                                      →

TTCAAGATATCATTGCGAAATTTCCGGTCCATCTTATCATGGGAATTAAAAAACCACTCC   180
 F  K  I  S  L  R  N  F  R  S  I  L  S  W  E  L  K  N  H  S  -  60

ATTGTACCAACTCACTATACATTGCTGTATACAATCATGAGTAAACCAGAAGATTTGAAG   240
 I  V  P  T  H  Y  T  L  L  Y  T  I  M  S  K  P  E  D  L  K  -  80
                                   cb3→                    →

GTGGTTAAGAACTGTGCAAATACCACAAGATCATTTTGTGACCTCACAGATGAGTGGAGA   300
 V  V  K  N  C  A  N  T  T  R  S  F  C  D  L  T  D  E  W  R  - 100
 →

AGCACACACGAGGCCTATGTCATCGTCCTAGAAGGATTCAGCGGGAACACAACGTTGTTC   360
 S  T  H  E  A  Y  V  I  V  L  E  G  F  S  G  N  T  T  L  F  - 120

AGTTGCTCACACAATTTCTGGCTGGCCATAGACATGTCTTTTGAACCACCAGAGTTTGAG   420
 S  C  S  H  N  F  W  L  A  I  D  M  S  F  E  P  P  E  F  E  - 140

ATTGTTGGTTTTACCAACCACATTAATGTGATGGTGAAATTTCCATCTATTGTTGAGGAA   480
 I  V  G  F  T  N  H  I  N  V  M  V  K  F  P  S  I  V  E  E  - 160
                             cb7→

GAATTACAGTTTGATTTATCTCTCGTCATTGAAGAACAGTCAGAGGGAATTGTTAAGAAG   540
 E  L  Q  F  D  L  S  L  V  I  E  E  Q  S  E  G  I  V  K  K  - 180
 →

CATAAACCCGAAATAAAAGGAAACATGAGTGGAAATTTCACCTATATCATTGACAAGTTA   600
 H  K  P  E  I  K  G  N  M  S  G  N  F  T  Y  I  I  D  K  L  - 200
                         cb6→                              →

ATTCCAAACACGAACTACTGTGTATCTGTTTATTTAGAGCACAGTGATGAGCAAGCAGTA   660
 I  P  N  T  N  Y  C  V  S  V  Y  L  E  H  S  D  E  Q  A  V  - 220
 →

ATAAAGTCTCCCTTAAAATGCACCCTCCTTCCACCTGGCCAGGAATCAGAATCAGCAGAA   720
 I  K  S  P  L  K  C  T  L  L  P  P  G  Q  E  S  E  S  A  E  - 240

TCTGCCAAAATAGGAGGAATAATTACTGTGTTTUGATAGCATTGGTCTTGACAAGCACC   780
 S  A  K  I  G  G  I  I  T  V  F  L  I  A  L  V  L  T  S  T  - 260
        tm

ATAGTGACACTGAAA.........................................     795
 I  V  T  L  K  .........................................   - 265
```

FIG. 4

```
GCTTTTGTCCCCCGCCCGCCGCTTCTGTCCGAGAGGCCGCCCGCGAGGCGCATCCTGACC    60
GCGAGCGTCGGGTCCCAGAGCCGGGCGCGGCTGGGGCCCGAGGCTAGCATCTCTCGGGAG   120
CCGCAAGGCGAGAGCTGCAAAGTTTAATTAGACACTTCAGAATTTTGATCACCTAATGTT   180

GATTTCAGATGTAAAAGTCAAGAGAAGACTCTAAAAATAGCAAAGATGCTTTTGAGCCAG   240
                                              M  L  L  S  Q     5

AATGCCTTCATCGTCAGATCACTTAATTTGGTTCTCATGGTGTATATCAGCCTCGTGTTT   300
 N  A  F  I  V  R  S  L  N  L  V  L  M  V  Y  I  S  L  V  F    25

GGTATTTCATATGATTCGCCTGATTACACAGATGAATCTTGCACTTTCAAGATATCATTG   360
 G  I  S  Y  D  S  P  D  Y  T  D  E  S  C  T  F  K  I  S  L    45

CGAAATTTCCGGTCCATCTTATCATGGAATTAAAAAACCACTCCATTGTACCAACTCAC   420
 R  N  F  R  S  I  L  S  W  E  L  K  N  H  S  I  V  P  T  H    65
                               *  *  *

TATACATTGCTGTATACAATCATGAGTAAACCAGAAGATTTGAAGGTGGTTAAGAACTGT   480
 Y  T  L  L  Y  T  I  M  S  K  P  E  D  L  K  V  V  K  N  C    85

GCAAATACCACAAGATCATTTTGTGACCTCACAGATGAGTGGAGAAGCACACACGAGGCC   540
 A  N  T  T  R  S  F  C  D  L  T  D  E  W  R  S  T  H  E  A   105
    *  *  *

TATGTCACCGTCCTAGAAGGATTCAGCGGGAACACAACGTTGTTCAGTTGCTCACACAAT   600
 Y  V  T  V  L  E  G  F  S  G  N  T  T  L  F  S  C  S  H  N   125
                            *  *  *

TTCTGGCTGGCCATAGACATGTCTTTTGAACCACCAGAGTTTGAGATTGTTGGTTTTACC   660
 F  W  L  A  I  D  M  S  F  E  P  P  E  F  E  I  V  G  F  T   145

AACCACATTAATGTGATGGTGAAATTTCCATCTATTGTTGAGGAAGAATTACAGTTTGAT   720
 N  H  I  N  V  M  V  K  F  P  S  I  V  E  E  E  L  Q  F  D   165

TTATCTCTCGTCATTGAAGAACAGTCAGAGGGAATTGTTAAGAAGCATAAACCCGAAATA   780
 L  S  L  V  I  E  E  Q  S  E  G  I  V  K  K  H  K  P  E  I   185

AAAGGAAACATGAGTGGAAATTTCACCTATATCATTGACAAGTTAATTCCAAACACGAAC   840
 K  G  N  M  S  G  N  F  T  Y  I  I  D  K  L  I  P  N  T  N   205
       *  *  *        *  *  *

TACTGTGTATCTGTTTATTTAGAGCACAGtGATGAGCAAGCAGTAATAAAGTCTCCCTTA   900
 Y  C  V  S  V  Y  L  E  H  S  D  E  Q  A  V  I  K  S  P  L   225

AAATGCACCCTCCTTCCACCTGGCCAGGAATCAGAATCAGCAGAATCTGCCAAAATAGGA   960
 K  C  T  L  L  P  P  G  Q  E  S  E  S  A  E  S  A  K  I  G   245

GGAATAATTACTGTGTTTTTGATAGCATTGGTCTTGACAAGCACCATAGTGACACTGAAA  1020
 G  I  I  T  V  F  L  I  A  L  V  L  T  S  T  I  V  T  L  K   265

TGGATTGGTTATATATGCTTAAGAAATAGCCTCCCCAAAGTCTTGAGGCAAGGTCTCACT  1080
 W  I  G  Y  I  C  L  R  N  S  L  P  K  V  L  R  Q  G  L  T   285

AAGGGCTGGAATGCAGTGGCTATTCACAGGTGCAGTCATAATGCACTACAGTCTGAAACT  1140
 K  G  W  N  A  V  A  I  H  R  C  S  H  N  A  L  Q  S  E  T   305

CCTGAGCTCAAACAGTCGTCCTGCCTAAGCTTCCCCAGTAGCTGGGATTACAAGCGTGCA  1200
 P  E  L  K  Q  S  S  C  L  S  F  P  S  S  W  D  Y  K  R  A   325

TCCCTGTGCCCCAGTGATTAAGTTTTATTATGTAGAAAATAAAGAGCAAACAGTTACAAA  1260
 S  L  C  P  S  D                                              331

AGAAAAAAAAAAAAAAAAAAAAAAAAAAAAAAAAAA                           1296
```

FIG. 5

```
   1  ATGCTTTTGAGCCAGAATGCCTTCATCTTCAGATCACTTAATTTGGTTCTCATGGTGTAT
   1  M  L  L  S  Q  N  A  F  I  F  R  S  L  N  L  V  L  M  V  Y  -

61  ATCAGCCTCGTGTTTGGTATTTCATATGATTCGCCTGATTACACAGATGAATCTTGCACT
  21  I  S  L  V  F  G  I  S  Y  D  S  P  D  Y  T  D  E  S  C  T  -

121  TTCAAGATATCATTGCGAAATTTCCGGTCCATCTTATCATGGAATTAAAAAACCACTCC
  41  F  K  I  S  L  R  N  F  R  S  I  L  S  W  E  L  K  N  H  S  -
                        *  *  *

181  ATTGTACCAACTCACTATACATTGCTGTATACAATCATGAGTAAACCAGAAGATTTGAAG
  61  I  V  P  T  H  Y  T  L  L  Y  T  I  M  S  K  P  E  D  L  K  -

241  GTGGTTAAGAACTGTGCAAATACCACAAGATCATTTTGTGACCTCACAGATGAGTGGAGA
  81  V  V  K  N  C  A  N  T  T  R  S  F  C  D  L  T  D  E  W  R  -
                     *  *  *

301  AGCACACACGAGGCCTATGTCACCGTCCTAGAAGGATTCAGCGGGAACACAACGTTGTTC
 101  S  T  H  E  A  Y  V  T  V  L  E  G  F  S  G  N  T  T  L  F  -
                                                *  *  *

361  AGTTGCTCACACAATTTCTGGCTGGCCATAGACATGTCTTTTGAACCACCAGAGTTTGAG
 121  S  C  S  H  N  F  W  L  A  I  D  M  S  F  E  P  P  E  F  E  -

421  ATTGTTGGTTTTACCAACCACATTAATGTGATGGTGAAATTTCCATCTATTGTTGAGGAA
 141  I  V  G  F  T  N  H  I  N  V  M  V  K  F  P  S  I  V  E  E  -

481  GAATTACAGTTTGATTTATCTCTCGTCATTGAAGAACAGTCAGAGGGAATTGTTAAGAAG
 161  E  L  Q  F  D  L  S  L  V  I  E  E  Q  S  E  G  I  V  K  K  -

541  CATAAACCCGAAATAAAAGGAAACATGAGTGGAAATTTCACCTATATCATTGACAAGTTA
 181  H  K  P  E  I  K  G  N  M  S  G  N  F  T  Y  I  I  D  K  L  -
                           *  *  *     *  *  *

601  ATTCCAAACACGAACTACTGTGTATCTGTTTATTTAGAGCACAGTGATGAGCAAGCAGTA
 201  I  P  N  T  N  Y  C  V  S  V  Y  L  E  H  S  D  E  Q  A  V  -

661  ATAAAGTCTCCCTTAAAATGCACCCTCCTTCCACCTGGCCAGGAATCAGAATTTTCATAA
 221  I  K  S  P  L  K  C  T  L  L  P  P  G  Q  E  S  E  F  S  *  -

721  CTTTTTAGCCTGGCCATTTCCTAACCTGCCACCGTTGGAAGCCATGGATATGGTGGAGGT
 781  CATTTACATCAACAGAAAGAAGAAAGTGTGGGATTATAATTATGATGATGAAAGTGATAG
 841  CGATACTGAGGCAGCGCCCAGGACAAGTGGCGGTGGCTATACCATGCATGGACTGACTGT
 901  CAGGCCTCTGGGTCAGGCCTCTGTCATCTCTACAGAATCCCAGTTGATAGACCCGGAGTC
 961  CGAGGAGGAGCCTGAACTGCCTGAGGTTGATGTGGAGCTCCCCACGATGCCAAAGGACAG
1021  CCCTCAGCAGTTGGAACTCTTGAGTGGGCCCTGTGAGAGGAGAAAGAGTCCACTCCAGGA
1081  CCCTCTTCCCGAAGAGGACTACAGCTCCACGGGGGGTCTGGGGGCAGAATCACCTTCAA
1141  TGTGGACTTAAACTCTGTGTTTTTGAGAGTTCTTGATGACGAGGACAGTGACGACTTAGA
1201  AGCCCCTCTGATGCTATCGTCTCATCTGGAAGAGATGGTTGACCCAGAGGATCCTGATAA
1261  TGTGCAATCAAACCATTTGCTGGCCAGCGGGGAAGGGACACAGCCAACCTTTCCCAGCCC
1321  CTCTTCAGAGGGCCTGTGGTCCAAGATGCTCCATCTGATCAAAGTGACACTTCTGAGTC
1381  AGATGTTGACCTTGGGGATGGTTATATAATGAGATGACTCCAAAACTATTGAATGAACTT
1441  GGACAGACAAGCACCTACAGGGTTCTTTGTCTCTGCATCCTAACTTGCTGCCTTATCGTC
1501  TGCAAGTGTTCTCCAAGGGAAGGAGGAGGAAACTGTGGTGTTCCTTTCTTCCAGGTGACA
1561  TCACCTATGCACATTCCCAGTATGGGGACCATAGTATCATTCAGTGGCATTGTTTTACAA
1621  TATTCAAAAGGTGGGCGCCAATTTTGGAAGGGAAGGAACATGTGCAACCTT
```

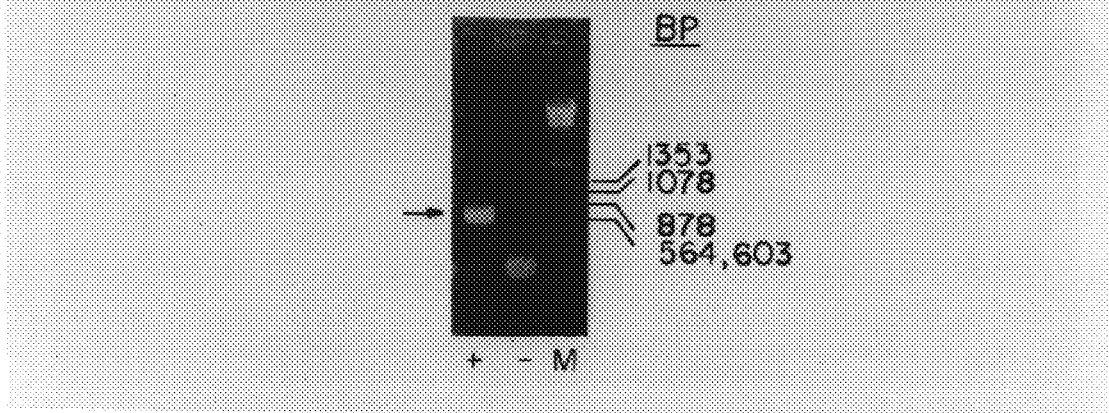

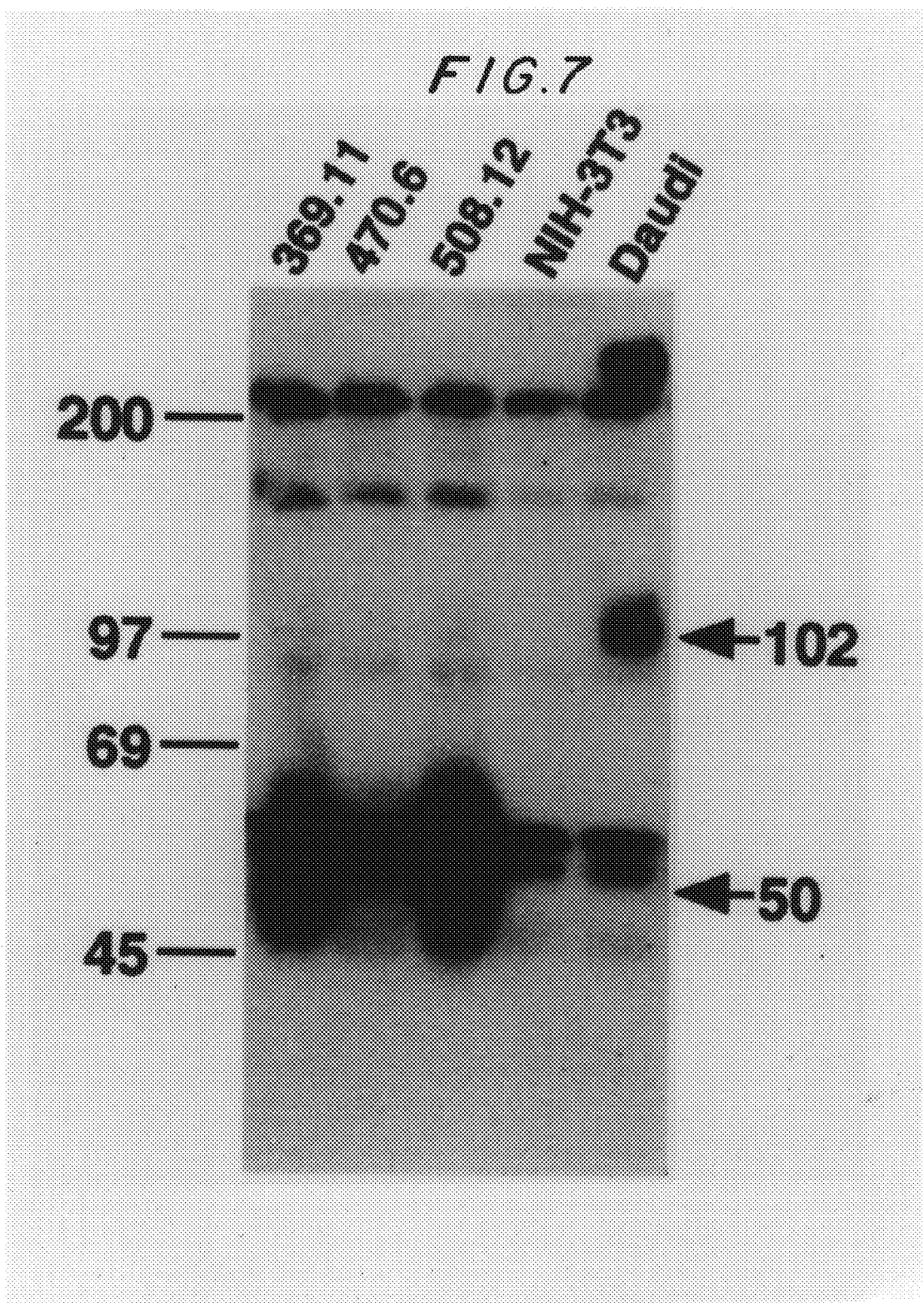

INTERFERON-α/β BINDING PROTEIN, ITS PREPARATION AND USE

CROSS-REFERENCE TO RELATED APPLICATION

The present application is a divisional of U.S. application Ser. No. 08/385,191 filed Feb. 7, 1995, now U.S. Pat. No. 5,821,078, which was a continuation-in-part of U.S. application Ser. No. 08/115,741 filed Sep. 3, 1993, now abandoned, the entire contents of which are hereby incorporated by reference.

FIELD OF THE INVENTION

The present invention relates to novel interferon-α/β binding proteins, capable of modulating the activity of various IFN-α subtypes, as well as IFN-β. More particularly, this invention relates to the cloning of DNA molecules coding for these proteins, their expression in host cells and to antibodies against these proteins.

Grandparent U.S. application Ser. No. 08/115,741 now abandoned describes a soluble IFN-α receptor protein of molecular weight of about 45,000, identified by Western blotting with monoclonal anti-IFN-α receptor antibodies. The above application also describes a different soluble IFN-α binding protein, having a molecular weight of about 40,000, that was identified by crosslinking with $^{125}$I-IFN-α and immuno-precipitation with anti-IFN-α monoclonal antibodies. When obtained from serum, this species had a molecular weight of 50K. The aforesaid 40,000 IFN-α binding protein, (hereinafter "urinary IFNAB-BP" or "IFNAB-BPII") is obtained from urine in a homogenous state and has a sequence that differs from any other known protein. The IFNAB-BP binds to and blocks the activity of a variety of different IFN-α subtypes, as well as IFN-β. In this respect, the binding characteristics of IFNAB-BP is significantly different from a previously described cell surface interferon receptor that binds only human interferon alpha B.

In accordance with the present invention, two cDNA molecules coding for precursors of IFNAB-BP are cloned and their sequence is determined. Both are probably derived from the same gene, e.g., by alternative splicing. Production of two recombinant proteins, designated IFNAB-BPI and IFNAB-BPII, in mammalian and other host cells is also described. Polyclonal and monoclonal antibodies directed against IFNAB-BP and useful for blocking the IFN receptor, for immunoassays and immunopurification of IFNAB-BPI and IFNAB-BPII are also disclosed.

IFNAB-BPI and IFNAB-BPII are capable of modulating the activity of type I interferons, i.e., the various subtypes of interferon-α, as well as interferon-β. Thus they may inhibit undesired effects of type I interferons.

BACKGROUND OF THE INVENTION

Type I interferons (IFNs) (IFN-α, IFN-β and IFN-ω) constitute a family of structurally related cytokines, usually defined by their ability to confer resistance to viral infections. Many other biological activities of type I IFNs have been reported, including inhibition of cell proliferation, induction of class I MHC antigens and several other immunoregulatory activities (1). IFN-α and IFN-β are useful for the treatment of several viral diseases, including hepatitis-C (2,3) and viral warts (4,5), as well as certain malignancies such as hairy cell leukemia (6), chronic myelogenous leukemia (7) and Kaposi's sarcoma (8).

IFN-α was detected in sera of various patients having autoimmune diseases such as systemic lupus erythematosus (9), as well as AIDS patients (10). IFN-α was implicated in the progression of juvenile diabetes (11). There has also been a report that increased expression of IFN-A in the white matter microglia may contribute to Alzheimer's disease pathology (51). Further, IFN-α therapy has been shown in some cases to lead to undesired side effects, including fever and neurological disorders (12). Hence there are pathological situations in which neutralization of IFN-α activity may be beneficial to the patient.

As in the case of other cytokines, IFN-α exerts its biological activities by binding to a cell surface receptor, which is specific for all IFN-α subtypes, as well as for IFN-β (13). A human IFN-α receptor was identified and cloned from Daudi cells (14). The cloned receptor has a single transmembrane domain, an extracellular and an intracellular domain. When expressed in murine cells, this receptor confers responsiveness to human IFN-αβ, but not significantly to other IFN-α and IFN-β species, indicating that additional components may be involved in the response to IFNβ and to various IFN-α subtypes.

Several other studies indicate that there are additional components or receptor subunits involved in the binding of IFN-α and IFN-β (15–17). Furthermore, it was reported that the already described receptor (14) is involved in binding of all IFN-α and IFN-β species (18).

Cytokine binding proteins (soluble cytokine receptors) correspond to the extracellular ligand binding domains of their respective cell surface cytokine receptors. They are derived either by alternative splicing of a pre-mRNA common to the cell surface receptor, or by proteolytic cleavage of the cell surface receptor. Such soluble receptors have been described in the past, including among others, the soluble receptors of IL-6 and IFN-γ (19–21), TNF (22–24), IL-1 (25–27), IL-4 (25,28), IL-2 (29,30), IL-7 (31) and IFN-alpha (32).

SUMMARY OF THE INVENTION

The present invention provides DNA molecules encoding the IFN-α/β binding protein. Such DNA molecules actually encode two distinct proteins, IFNAB-BPI and IFNAB-BPII, probably derived from the same pre-mRNA by alternative splicing, to yield two mRNA molecules, one having a size of about 1.5 kb and the other a size of about 4.5 kb, each of which encodes one of the binding proteins, the 1.5 kb mRNA encoding the IFNAB-BPI and the 4.5 kb mRNA encoding the IFNAB-BP. The term IFNAB-PB corresponds to both IFNAB-BPI and IFNAB-BPII. Urinary IFNAB-BP is identified as IFNAB-BPII.

Accordingly, the present invention provides a DNA molecule encoding an IFN-α/β binding protein selected from IFNAB-BPI, IFNAB-BPII, fused proteins and muteins of IFNAB-BPI and IFNAB-BPII, their functional derivatives and their active fractions.

The invention further provides replicable expression vehicles containing said DNA molecules, hosts transformed therewith and proteins produced by such transformed hosts. The term "DNA molecules" includes genomic DNA, cDNA, synthetic DNA and combinations thereof.

The invention also relates to DNA molecules which hybridize under stringent conditions to the above DNA molecules and encode proteins having the same biological activity as the IFNAB-BPs.

The present invention also provides methods for preparation in host cells capable of production of a functional IFNAB-BPI and IFNAB-BPII, fused proteins, muteins or active fractions thereof.

The present invention also provides the recombinant IFNAB-BPI and IFNAB-BPII, fused proteins, muteins or active fractions thereof, and salts of all of same, and pharmaceutical compositions containing IFNAB-BPI or IFNAB-BPII, fused proteins, muteins, active fractions thereof, or salts of all of same.

IFNAB-BPI and IFNAB-BPII inhibit the biological activities of natural human leukocyte and fibroblast interferons, as well as recombinant human IFN-α2, IFN-αβ, IFN-αC and IFN-β. IFNAB-BPI corresponds to a novel transmembrane protein which is the ligand-binding IFN-α/β receptor. IFNAB-BPII is a soluble receptor, essentially corresponding to the extracellular, ligand-binding domain of IFNAB-BPI.

DESCRIPTION OF THE FIGURES

FIGS. 1A–C show the cloning strategy of IFNAB-BPI and IFNAB-BPII:
 (A) Middle row: The sequence of an internal CNBr peptide (residues 151–177 of SEQ ID NO:2, 27 amino acid residues, cb7) obtained from the urinary 40,000 IFNAB-BP.
  Top and bottom rows: Synthetic sense (SEQ ID NO:3, top) and antisense (SEQ ID NO:4, bottom), degenerate oligonucleotide mixtures, made on the basis of the peptide sequence and used for reverse transcription (antisense primer only) and for polymerase chain reaction (PCR).
 (B) Agarose gel electrophoresis of PCR products, made with the above sense and antisense primers. The following RNAs and primers were used for generating cDNA that was used as template for the PCR: (1) Poly A+RNA of Daudi cells; antisense primer. (2) Poly A+RNA of Daudi cells, oligo d(T) primer. (3) Total RNA of WISH cells, antisense primer. The size (bp) of the DNA markers is indicated on the left side.
 (C) Top row: The non-degenerate portion of the sequence (nucleotides 700–734 of SEQ ID NO:1), obtained from pBluescript clones of the 101 bp PCR product.
  Bottom row: Translation of the resulting non-degenerate DNA sequence into the expected sequence which is part of the sequence of peptide cb7 (residues 159–170 of SEQ ID NO:2).

FIG. 2 shows the cDNA (SEQ ID NO:13) and translated polypeptide sequence (SEQ ID NO:14) of clone q10, carrying the cDNA of IFNAB-BPI:
 This clone was isolated from a lambda gt11 library, made from cDNA of human HeLa cells, by screening with a synthetic oligonucleotide corresponding to the non-degenerate DNA sequence of FIG. 1(C). Sequences corresponding to the N-terminus of the urinary IFNAB-BP and to its CNBr peptides are underlined and the corresponding sequence name is given below the line (n1, N-terminus 1; n2, N-terminus 2; cb3, CNBr peptide 3; cb6, CNBr peptide 6; cb7, CNBr peptide 7). Hydrophobic sequences, corresponding to the signal peptide(s) and the transmembrane domain (tm) are double underlined. Bold numbers on the right side are those of the amino acid residues. Plain numbers correspond to nucleotide residues, taking the initator A of ATG as No. 1.

A 397 base pair (bp) probe, corresponding to nucleotides 218–614 of IFNAB-BPI was prepared by polymerase chain reaction with appropriate primers and [$^{32}$P] labeled by random primer labeling. Poly A+ RNA from human Daudi cells was analyzed by electrophoresis on agarose (1.5%), blotted onto nitrocellulose and hybridized with the specific probe. The size of the ribosomal RNA is indicated on the right side.

FIG. 4 shows nucleotide (SEQ ID NO:1) and amino acid (SEQ ID NO:2) sequences of a complete 1.5 kb cDNA clone corresponding to IFNAB-BPI. Amino acid residues in single letter codes are numbered in bold, starting at the translation-initation codon. Hydrophobic leader and transmembrane regions are underlined. N-terminal protein sequences of urinary IFNAB-BP (From codon 27) and the internal CNBr peptides are dot-underlined (however Cys and N-glycosylated Asn residues are not detectable). N-glycosylation signals are indicated by asterisks and the polyadenylation signal is double underlined.

FIG. 5 shows partial nucleotide (SEQ ID NO:5) and amino acid (SEQ ID NO:6) sequences of a 4.5 kb cDNA clone corresponding to IFNAB-BPII. Amino acid residues in single letter codes are numbered in bold, starting at the translation-initiation codon. The hydrophobic leader region is underlined. N-terminal protein sequences of urinary IFNAB-BP (from codon 27) and the internal CNBr peptides are dot-underlined (Cys and N-glycosylated Asn residues are not detectable). N-glycosylation signals and the stop codon are indicated by asterisks.

Figure 6C:
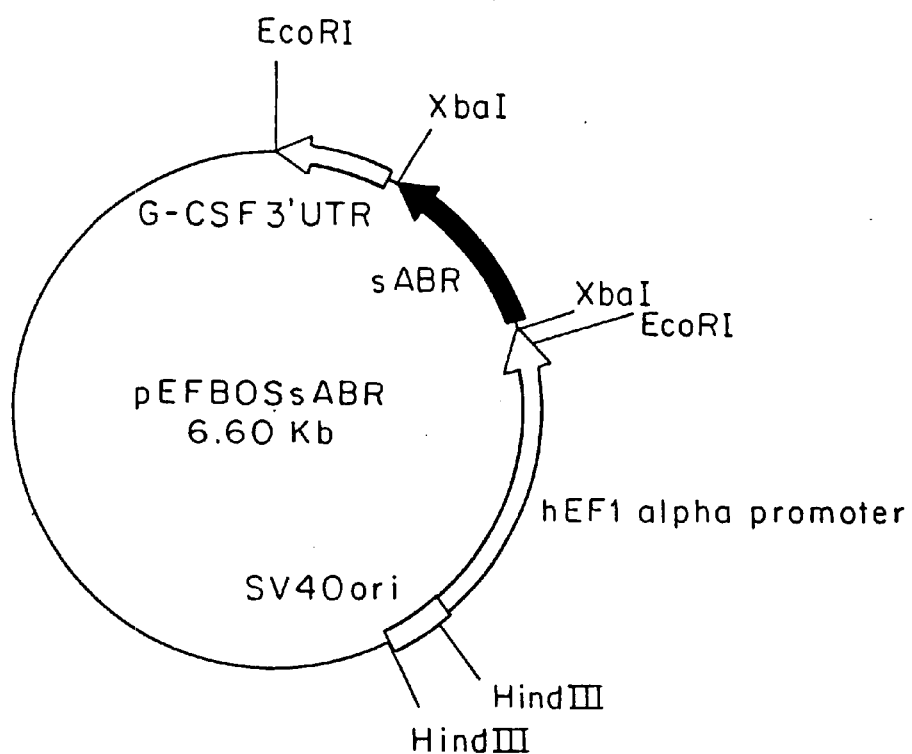

FIGS. 6A–C show the construction of a mammalian expression vector for expression of the extracellular, ligand-binding domain of IFNAB-BPI.
 (A) Sense (SEQ ID NO:7) and antisense (SEQ ID NO:8) synthetic oligonucleotides used for preparing the DNA that codes for the extracellular, ligand-binding domain of IFNAB-BPI by polymerase chain reaction.
 (B) Agarose gel electrophoresis of the 850 bp product of a polymerase chain reaction (PCR), made with the above sense and antisense primers and DNA of clone q10.
 (C) The structure of pEF-BOS-sIFNAB-BPI, a mammalian expression vector for production of a soluble IFNAB-BPI.

FIG. 7 shows the expression of IFNAB-BPI and IFNAR in various cells:
 Expression of IFNAB-BPI in various cells is shows by SDS-PAGE (7.5% acrylamide, non-reducing conditions) of detergent cell extracts, followed by immunoblotting with rabbit anti IFNAB-BPII antibody and $^{125}$I-protein A. Clone 369.11 is NIH-3T3 cells, expression IFNAB-BPI; Clone 470.6 is NIH-3T3 cells expression IFNAR; and Clone 508.12 expresses both proteins. Control NIH-3T3 cells and human Daudi cells are shown as well. The 51 kDa from (in murine cells) and 102 kDa form (in Daudi cells) of IFNAB-BPI are indicated by arrows. Molecular mass markers are shown on the left side.

Figure 8A:
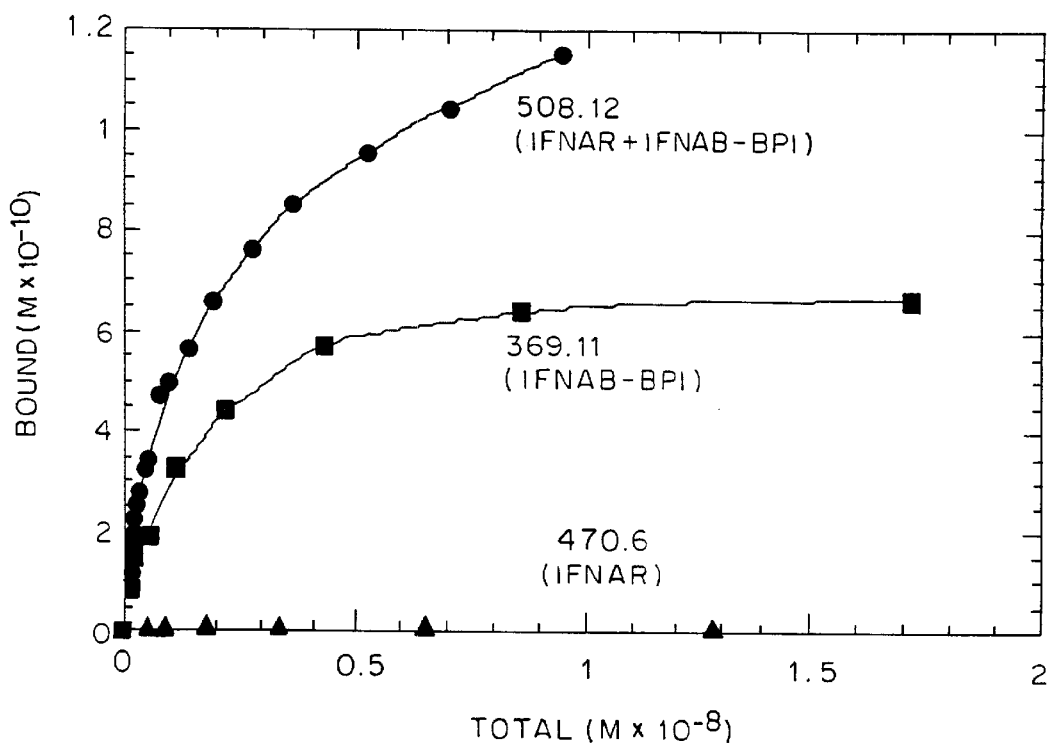
Figure 8B:
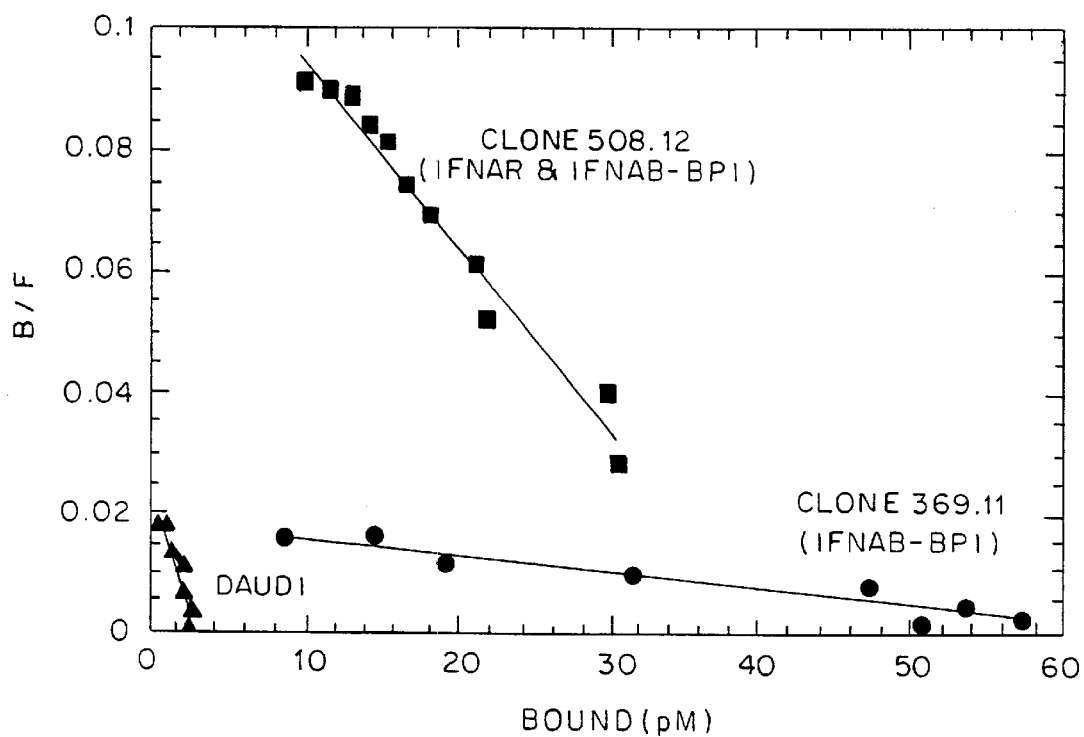

FIGS. 8A–B show binding of $^{123}$I-IFN-α2 to various host cells:
 (A) Saturation binding of $^{125}$I-IFN-α2 to NIH 3T3 cells expressing IFNAB-BPI (Clone 369.11, ■) and cells expressing both IFNAB-BPI and IFNAR (Clone 508.12, ●) and lack of binding to cells expressing IFNAR only (Clone 470.6, ▲). (B) Scatchard analysis of $^{125}$I-IFN-α2-binding to the above cells. Binding data were analyzed by the LIGAND program. The following cells showed high affinity saturable binding: huDaudi (▲), IFNAB-BPI-positive cells (Clone 369.11, ■) and Clone 508.12, expressing both IFNAR and IFNAB-BPI (▲).

Figure 9:
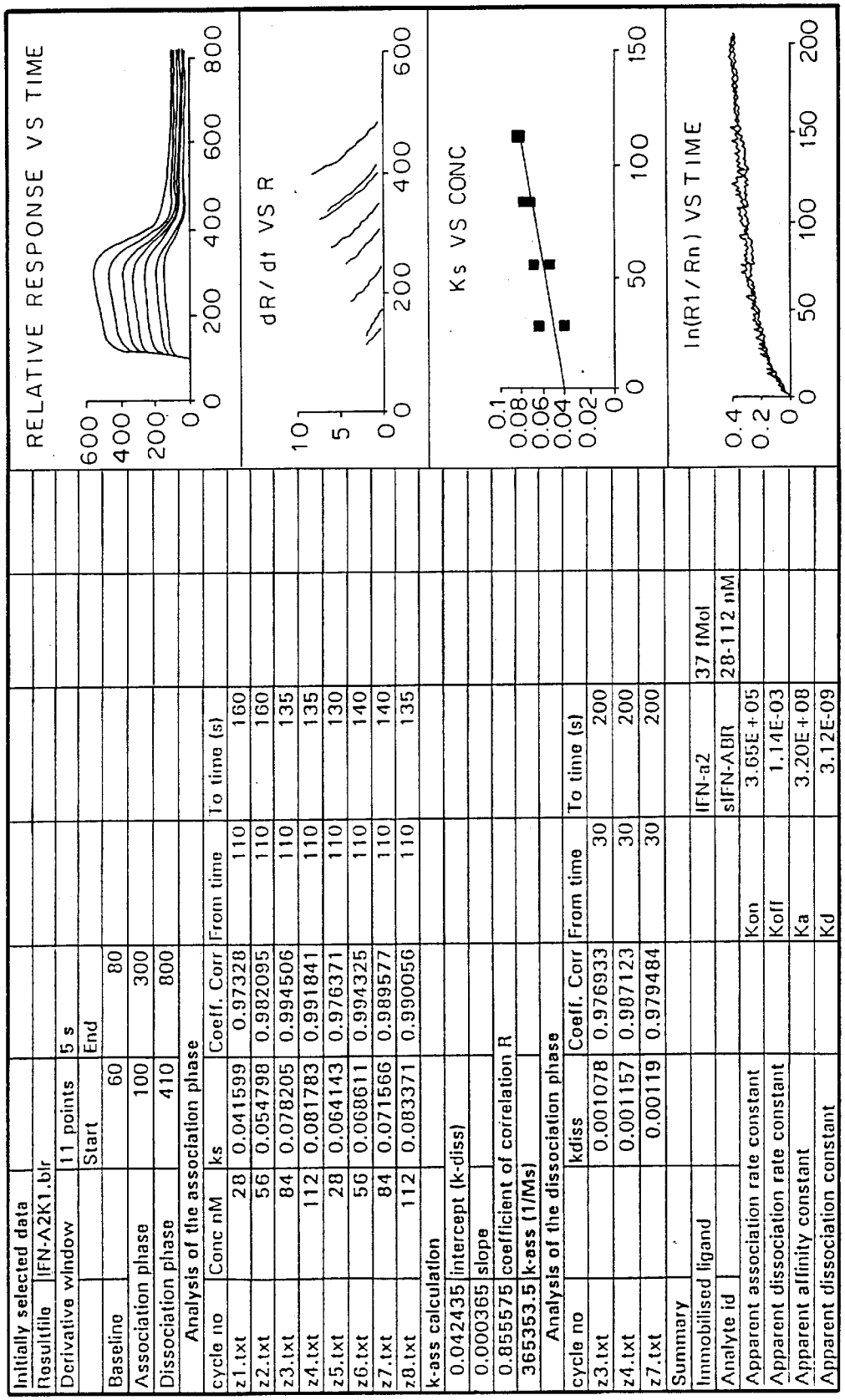

FIG. 9 summarizes the results of a study on a BIAcore system which determine the affinity of urinary IFNAB-BPII TO IFN-α2:

IFN-α2 was immobilized on the sensor chip and various concentrations of urinary IFNAB-BPII were passed through the sensor chip. "Relative response vs. time" shows the binding and dissociation process. The apparent dissociation constant is $3.12 \times 10^{-9}$ M.

Figure 10:
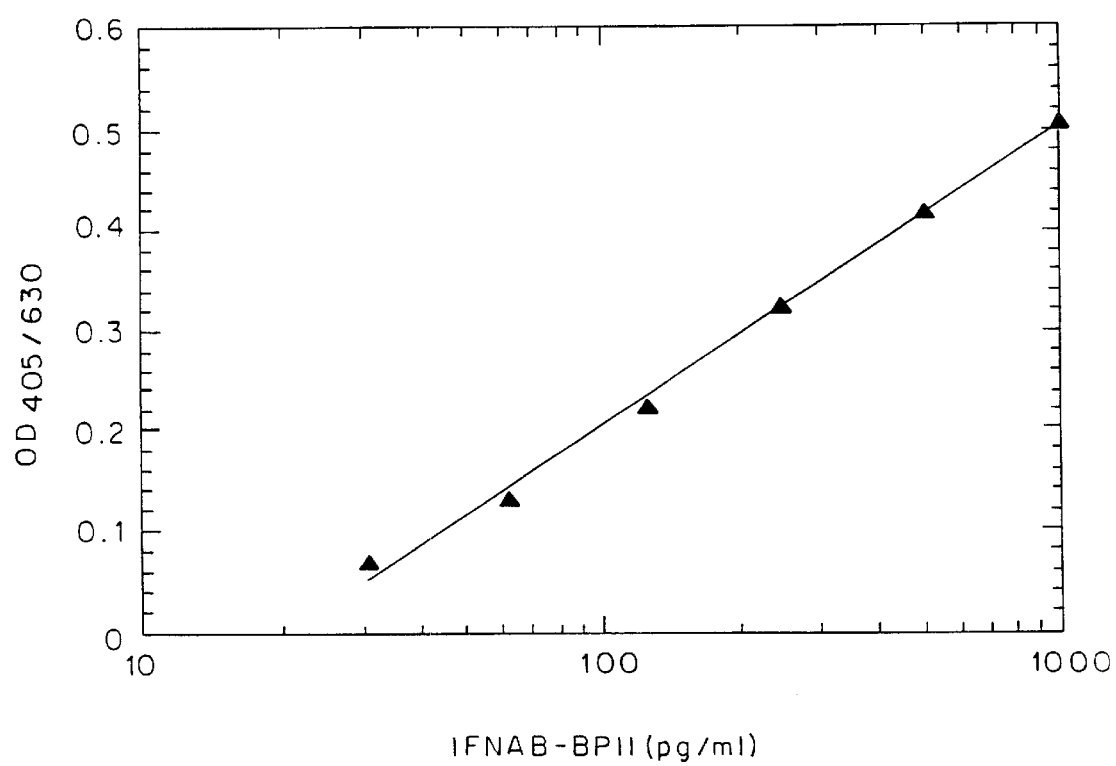

FIG. 10 shows an ELISA of urinary IFNAB-BPII:

Pure urinary IFNAB-BPII was diluted twofold serially to the indicated concentrations, added to microELISA plates that had been pre-coated with mab anti IFNAB-BPII antibody. The plates were then reacted with rabbit anti IFNAB-BPII antibody followed by a goat anti-rabbit horseradish peroxidase conjugate and ABTS/$H_2O_2$ substrate. The plates were read at 405/630 nm. The lower limit of detection is 30 pg/ml.

DETAILED DESCRIPTION OF THE INVENTION

According to grandparent application Ser. No. 08/115,741 now abandoned, an IFN-α/β binding protein having a molecular weight of 40,000 (IFNAB-BP) was isolated from normal urine by two chromatographic steps. Crude urinary proteins were loaded on a column consisting of IFN-α2 bound to agarose. The column was washed to remove nonrelevant proteins and the bound proteins were then eluted at low pH. Eluted proteins were then resolved by size exclusion HPLC to give several protein peaks, one of which was characterized by its ability to react specifically with $^{125}$I-IFN-α2 and to block the antiviral activity of IFN-α and IFN-β. This protein was further characterized by N-terminal microsequence analysis, which gave a major sequence at its N-terminal domain:

Asp-Ser-Pro-Asp-Tyr-Thr-Asp-Glu-Ser-Arg-Thr-Phe-Lys-Ile-Arg-Leu-Arg (SEQ ID NO:9)

A minor polypeptide sequence, corresponding to the major sequence, but having three extra amino acid residues (Ile-xxx-Tyr) at the N-terminus of the above sequence, was detected (xxx denotes an unidentified amino acid). The resulting sequence was compared with and found to be completely different from that of the known IFN-α receptor (14). It was also different from any other known protein and it was not coded by any known DNA sequence, as determined by comparing it to Swissprot and Genebank data libraries, using the FastA program (33).

A sample of the urinary IFNAB-BP was digested with CNBr, resolved on SDS-PAGE, electroblotted onto a PVDF membrane and the resulting digestion fragments were subjected to protein microsequencing. One of the fragments had a molecular weight of less than 1OK and an internal sequence as follows (Met precedes the actual sequence):

Met-Val-Lys-Phe-Pro-Ser-Ile-Val-Glu-Glu-Glu-Leu-Gln-Phe-Asp-Leu-Ser-Leu-Val-Ile-Glu-Glu-Gln-Ser-Glu-Gly-Ile (residues 151–177 of SEQ ID NO:2, 27 residues).

This internal sequence, was reverse-translated into sense and antisense primers to which suitable restriction sites were added. Total RNA was purified from human cells and first strand cDNA was generated with reverse transcriptase, using either the antisense oligonucleotide mixture or oligo d(T) as a primer. The resulting cDNA fragment was then amplified in a polymerase chain reaction (PCR), using the combined sense and antisense degenerate primers. Analysis of the PCR products on a 3% agarose gel showed a specific 101 bp oligonucleotide band. This DNA was restriction-digested, cloned into pBluescript (Stratagene) and competent E. coli were transfected with this vector. Several independent clones were sequenced. The sequence of the region flanked by the sense and antisense degenerate primers was invariant and encoded the expected sequence from the above mentioned CNBr peptide (cb7) of urinary IFNAB-BP. An oligonucleotide corresponding to this non-degenerate internal sequence was synthesized, end-labeled and used for screening of cDNA libraries.

Screening of a lambda gt11 cDNA library of human HeLa cells (Clontech) gave several positive clones. One of these clones designated q10, had an open reading frame that corresponded to a signal peptide, an extracellular domain, a transmembrane domain and a short cytoplasmic domain. The peptide sequences obtained from the urinary IFNAB-BP were all present within the extracellular domain encoded by q10. A few amino acid residues of the peptide sequence were incorrect due to limitation of the protein sequencing technology (mainly the inability to identify Cys and the low levels of peaks corresponding to Ser).

Sense and antisense primers, corresponding to ends of the nucleotide sequence 219–613 of clone q10 (FIG. 2) were used for preparing a specific probe by PCR, using clone q10 as a DNA template. The resulting DNA was labeled with [$^{32}$P] and used for Northern blot hybridization of poly A+ mRNA from two human cell lines. In both cases two specific bands were observed, one corresponding to 1.5 kb mRNA and another one, corresponding to 4.5 kb mRNA. The primary translation product of the 1.5 kb mRNA is designated as IFNAB-BPI precursor. The primary translation of the product of the 4.5 kb mRNA is designated as IFNAB-BPII precursor.

The aforementioned specific probe was used for screening an additional human cDNA library and two groups of cDNA clones were identified. One group (about 20 individual clones) had a length of 1.5 kb and coded for the same precursor of the transmembrane protein that was coded by clone q10. The second group (2 individual clones) had a length of 4.5 kb. These sizes were the same as those of the two mRNA species, and therefore the 1.5 kb cDNA clones coded for IFNAB-BPI while the 4.5 kb cDNA clones coded for IFNAB-BPII. Sequencing of the 4.5 kb clones indicated that they code for a precursor of a truncated soluble receptor corresponding to codons 1–239 of clone q10. However codons 238 and 239 were different and were followed by a stop codon. Protein sequence analysis of the C- terminus of the urinary 40,000 IFNAB-BP was identified as IFNAB-BPII. "Precursor" as used herein, is defined as the primary translation product which includes the signal peptide.

DNA coding for the precursor of a truncated soluble form of IFNAB-BPI was generated by PCR. The resulting PCR product was inserted into a mammalian expression vector and used for transfection of various mammalian cells, such as monkey COS cells. Such cells expressed high levels of biologically active recombinant IFNAB-BPI.

Similarly, DNA coding for the precursor of IFNAB-BPII was generated by PCR. The resulting PCR product was inserted into a mammalian expression vector and used for transfection of various mammalian cells, such as monkey COS cells. Such cells expressed high levels of biologically active recombinant IFNAB-BPII. Similarly, DNA coding for the entire precursor of IFNAB-BPI was generated by PCR. The resulting PCR product was inserted into a mammalian expression vector and used for transfection of various mammalian cells, such as mouse NIH-3T3 cells. Such cells expressed high levels of human IFNAB-BPI. The cells were able to bind human IFN-α2 with a high affinity (Kd=3.6× $10^{-9}$ M). When both human IFNAB-BPI and the previously cloned human IFN-αB receptor INFAR (14) were co-expressed in mouse NIH-3T3 cells the affinity of the composite receptor was increased by about 10-fold (Kd=4× $10^{-10}$ M). In contrast, when only human IFNAR was expressed in mouse cells no binding of human IFN-α2 could be demonstrated. Therefore, a composite protein containing two attached polypeptides, one of which having the ligand binding domain of IFNAB-BPI or IFNAB-BPII, and the second polypeptide having the extracellular domain of IFNAR, will exhibit a higher affinity for IFN-α as compared with IFNAB-BPI or IFNAB-BPII alone.

The affinity of the urinary IFNAB-BPII for human IFN-α2 was determined by the BIAcore system (Pharmacia, Sweden). IFN-α2 was immobilized on sensor chip and allowed to bind IFNAB-BPII. Based on Kon and Koff values, a Kd value of $3.12\times10^{-9}$ M was obtained. This value is very close to the one obtained with NIH-3T3 cells expressing IFNAB-BPI.

The above-mentioned cloning, clone isolation, identification, characterization and sequencing procedures are described in more detail hereinafter in the Examples.

IFNAB-BPI and IFNAB-BPII can also be produced by other types of recombinant cells such as prokaryotic cells, e.g., *E. coli*, or other eukaryotic cells, such as CHO, yeast or insect cells. Methods for constructing appropriate vectors, carrying DNA that codes for either IFNAB-BPI or IFNAB-BPII and suitable for transforming (e.g., *E. coli* and yeast cells) or infecting insect cells in order to produce recombinant IFNAB-BPI and IFNAB-BPII are well known in the art. See, for example, Ausubel et al., eds. "Current Protocols in Molecular Biology" *Current Protocols*, 1993; and Sambrook et al., eds,. "Molecular Cloning: A Laboratory Manual", 2nd Ed., Cold Spring Harbor Press, 1989.

The invention further relates to active muteins and fragments of IFNAB-BPI and IFNAB-BPII and to fused proteins consisting of wild type IFNAB-BPI or IFNAB-BPII, or their active muteins or their active fractions, fused to another polypeptide or protein and exhibiting a similar ability to block the biological activities of IFN-α and IFN-β or other cytokines which share the interferon alpha/beta receptor.

DNA encoding IFNAB-BPI or IFNAB-BPII, their fragments, muteins or fused proteins, and the operably linked transcriptional and translational regulatory signals, are inserted into eukaryotic vectors which are capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototrophy to an auxotropic host, biocide resistance, e.g., antibiotics, or resistance to heavy metals, such as copper, or the like. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals (34).

For the purposes of expression of the IFNAB-BPI and IFNAB-BPII proteins, their active fractions or derivatives, the DNA molecule to be introduced into the cells of choice will preferably be incorporated into a plasmid or viral vector capable of autonomous replication in the recipient host.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli*, for example, pBR322, ColE1, pSC101, pACYC 184, etc. (35); Bacillus plasmids such as pC194, pC221, pT127, etc. (36); Streptomyces plasmids including pIJ101 (37), Streptomyces bacteriophages such as ΦC31 (38) and Pseudomonas plasmids (39,40) Preferred eukaryotic plasmids include BPV, vaccinia, SV40, 2-micron circle, etc., or their derivatives. Such plasmids are well known in the art (41–45).

Once the vector or DNA sequence containing the construct(s) has been prepared for expression, the expression vector may be introduced into an appropriate host cell by any of a variety of suitable means, such as transformation, transfection, lipofection, conjugation, protoplast fusion, electroporation, calcium phosphate precipitation, direct microinjection, etc.

Host cells to be used in this invention may be either prokaryotic or eukaryotic. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F⁻, lambda⁻, phototropic (ATCC 27325)), and other enterobacteria such as *Salmonella typhimurium* or *Serratia narcescens* and various Pseudomonas species. Under such conditions, the protein will not be glycosylated. The prokaryotic host must be compatible with the replicon and control sequences in the expression plasmid.

However, since IFNAB-BPI and IFNAB-BPII are glycosylated proteins, eukaryotic hosts are preferred over prokaryotic hosts. Preferred eukaryotic hosts are mammalian cells, e.g., human, monkey, mouse and Chinese hamster ovary (CHO) cells, because they provide post-translational modifications to protein molecules including correct folding, correct disulfide bond formation as well as glycosylation at correct sites. Also yeast cells and insect cells can carry out post-translational peptide modifications including high mannose glycosylation. A number of recombinant DNA strategies exist which utilize strong promoter sequences and high copy number of plasmids which can be utilized for production of the desired proteins in yeast and in insect cells. Yeast cells recognize leader sequences on cloned mammalian gene products and secrete peptides bearing leader sequences. After the introduction of the vector, the host cells are grown in a selective medium, which selects for the growth of vector-containing cells. Expression of the cloned gene sequence(s) results in the production of IFNAB-BPI or IFNAB-BPII, fusion proteins, or muteins or fragments thereof. The expressed proteins are then isolated and purified by any conventional procedure involving extraction, precipitation, chromatography, electrophoresis, or the like, or by affinity chromatography, using anti-IFNAB-BPI monoclonal antibodies immobilized on a gel matrix contained within a column. Crude preparations containing said recombinant IFNAB-BPI or IFNAB-BPII are passed through the column whereby IFNAB-BPI or IFNAB-BPII, their active fractions and derivatives will be bound to the column by the specific antibody while the impurities will pass through. After washing, the protein is eluted from the gel under conditions usually employed for this purpose, i.e., at a high or a low pH, e.g., pH 11 or pH 2.

As used herein the term "muteins" refers to analogs of IFNAB-BPI or IFNAB-BPII, in which one or more of the amino acid residues of the natural IFNAB-BPI or IFNAB-BPII or their active fractions are replaced by different amino acid residues, or are deleted, or one or more amino acid residues are added to the natural sequence of IFNAB-BPI or IFNAB-BPII, without changing considerably the activity of the resulting products as compared with wild type IFNAB-BPI or IFNAB-BPII or their active fractions. These muteins are prepared by known synthesis and/or by site-directed mutagenesis techniques, or any other known technique suitable therefor.

Any such mutein preferably has a sequence of amino acids sufficiently duplicative of those of IFNAB-BPI and IFNAB-BPII such as to have substantially similar activity to IFNAB-BPI and IFNAB-BPII. One activity of IFNAB-BPI and IFNAB-BPII is its capability of binding to one or more type I interferons, such as natural human leukocyte and fibroblast interferons as well as recombinant human IFN-α2, IFN-αB, IFN-αC and IFN-β. As long as the mutein has substantial binding activity to one or more of such interferons, it can be used in the purification of such interferons, such as by means of affinity chromatography, and thus can be considered to have substantially similar activity to IFNAB-BPI and IFNAB-BPII. Thus, it can be determined whether any given mutein has substantially the same activity as IFNAB-BPI or IFNAB-BPII by means of routine experimentation comprising subjecting such a mutein, e.g., to a simple sandwich competition assay to determine whether or not it binds to an appropriately labeled interferon, such as a radioimmunoassay or ELISA assay. This test should be repeated with several species of type I interferon, as a mutein which binds to any species of type I interferon retains sufficient activity of IFNAB-BPI or IFNAB-BPII has at least one of the disclosed utilities of IFNAB-BPI or IFNAB-BPII and thus has substantially similar activity thereto.

In a preferred embodiment, any such mutein has at least 40% identity or homology with the sequence of either a IFNAB-BPI or IFNAB-BPII. More preferably, it has at least 50%, at least 60%, at least 70%, at least 80% or, most preferably, at least 90% identity or homology thereto.

Muteins of IFNAB-BPI or IFNAB-BPII polypeptides or proteins which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. For a presentation of nucleotide sequence substitutions, such as codon preferences, see Ausubel et al, supra, at §§ A.1.1–A.1.24, and Sambrook et al, supra, at Appendices C and D.

Preferred changes for muteins in accordance with the present invention are what are known as "conservative" substitutions. Conservative amino acid substitutions of IFNAB-BPI and IFNAB-BPII polypeptides or proteins may include synonymous amino acids within a group which have sufficiently similar physicochemical properties that substitution between members of the group will preserve the biological function of the molecule, Grantham, *Science*, vol. 185, pgs. 862–864 (1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", *Science*, Vol. 181, pgs. 223–230 (1973). Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFNAB-BPI or IFNAB-BPII polypeptides or proteins or their active fractions for use in the present invention include any known method steps, such as presented in U.S. Pat. Nos. RE 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In another preferred embodiment of the present invention, any mutein of IFNAB-BPI or IFNAB-BPII or their active fractions has an amino acid sequence essentially corresponding to that of IFNAB-BPI or IFNAB-BPII. The term "essentially corresponding to" is intended to comprehend proteins with minor changes to the sequence of the natural protein which do not affect the basic characteristics of the natural proteins, particularly insofar as their ability to bind one or more type I interferons is concerned, and to thereby inhibit the binding of type I interferon to a natural type I interferon receptor in situ. The type of changes which are generally considered to fall within the "essentially corresponding to" language are those which would result from conventional mutagenesis techniques of the DNA encoding these proteins, resulting in a few minor modifications, and screening for the desired activity in the manner discussed above.

Muteins in accordance with the present invention include proteins encoded by a nucleic acid, such as DNA or RNA, which hybridizes to DNA or RNA which encodes IFNAB-BPI or IFNAB-BPII in accordance with the present invention, under stringent conditions. The invention also includes such nucleic acid which is also useful as a probe in identification and purification of the desired nucleic acid. Furthermore, such nucleic acid would be a prime candidate to determine whether it encodes a polypeptide which retains the functional activity of the IFNAB-BP, IFNAB-BPI or IFNAB-BPII of the present invention. The term "stringent conditions" refers to hybridization and subsequent washing conditions which those of ordinary skill in the art conventionally refer to as "stringent". See Ausubel et al., *Current Protocols in Molecular Biology*, supra, Interscience, N.Y., §§6.3 and 6.4 (1987, 1992), and Sambrook et al., supra. Without limitation, examples of stringent conditions include washing conditions 12–20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30–60 minutes and then a 0.1×SSC and 0.5% SDS at 68° C. for 30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See Ausubel, supra.

The term "fused protein" refers to a polypeptide comprising IFNAB-BPI or IFNAB-BPII or their active fractions or a mutein thereof, fused with another protein which, e.g., has an extended residence time in body fluids. IFNAB-BPI or IFNAB-BPII may thus be fused to another protein, polypeptide or the like, e.g., an immunoglobulin or a fragment thereof.

The term "salts" herein refers to both salts of carboxyl groups and to acid addition salts of amino groups of IFNAB-BPI, IFNAB-BPII, their active fractions, muteins, or fused proteins thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course any such salts must have substantially similar activity to IFNAB-BPI or IFNAB-BPII or their active fractions.

"Functional derivatives" as used herein cover derivatives of IFNAB-BPI or IFNAB-BPII or their active fractions and their muteins and fused proteins, which may be prepared from the functional groups which occur as side chains on the residues or the N- or C-terminal groups, by means known in the art, and are included in the invention as long as they remain pharmaceutically acceptable, i.e., they do not destroy the activity of the protein which is substantially similar to the activity of IFNAB-BPI, IFNAB-BPII, and do not confer toxic properties on compositions containing it. These derivatives may, for example, include polyethylene glycol sidechains which may mask antigenic sites and extend the residence of IFNAB-BPI or IFNAB-BPII in body fluids. Other derivatives include aliphatic esters of the carboxyl groups, amides of the carboxyl groups by reaction with ammonia or with primary or secondary amines, Na-cyl derivatives of free amino groups of the amino acid residues formed with acyl moieties (e.g., alkanoyl or carbocyclic aroyl groups) or O-acyl derivatives of free hydroxyl groups (for example that of seryl or threonyl residues) formed with acyl moieties.

As "active fractions" of IFNAB-BPI or IFNAB-BPII, muteins and fused proteins, the present invention covers any fragment or precursors of the polypeptide chain of the protein molecule, or fused proteins containing any such fragment of IFNAB-BPI or IFNAB-BPII, alone or together with associated molecules or residues linked thereto, e.g., sugar or phosphate residues, or aggregates of any of the above protein molecule, provided said fraction has substantially similar activity to IFNAB-BPI or IFNAB-BPII.

The present invention further relates to pharmaceutical compositions comprising a pharmaceutically acceptable carrier and IFNAB-BPI or IFNAB-BPII of the invention or their active muteins, fused proteins and their salts, functional derivatives or active fractions thereof.

The pharmaceutical compositions of the invention are prepared for administration by mixing IFNAB-BPI or IFNAB-BPII or their derivatives, with physiologically acceptable carriers, and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion.

As mentioned in grandparent application Ser. No. 08/115,741 now abandoned, the IFN-α/β binding protein (or herein designated IFNAB-BPII) inhibited the antiviral activity of IFN-α2, IFN-αB, IFN-αC and IFN-β and not IFN-γ, which indicates that IFNAB-BPI and IFNAB-BPII are general type I IFN binding proteins. Thus, these are useful for modulating or blocking the biological activities of IFN-α subtypes and IFN-β, for example in type I diabetes, various autoimmune diseases, graft rejections, AIDS and similar diseases, in which there is an aberrant expression of IFN-α or IFN-β, i.e., IFNAB-BPI and BPII may be used in any condition where an excess of IFN-α or IFN-β is endogenously produced or exogenously administered.

Accordingly, IFNAB-BPI and IFNAB-BPII, their active fractions, muteins, fused proteins and their salts, functional derivatives, and active fractions thereof are indicated for the treatment of autoimmune diseases, for other inflammations in mammals, for treatments of toxicity caused by administration of interferon alpha or beta, for juvenile diabetes, for lupus erythematosus and for AIDS.

As indicated above, the proteins of the present invention also have non-therapeutic utility such as in the purification of type I interferon species.

The invention also includes antibodies against IFNAB-BPI, IFNAB-BPII, their muteins, fused proteins, salts, functional derivatives and active fractions.

The term "antibody" is meant to include polyclonal antibodies, monoclonal antibodies (mabs), chimeric antibodies, anti-idiotypic (anti-Id) antibodies to antibodies that can be labeled in soluble or bound form, as well as active fractions thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, *Nature* 256:495–497 (1975); U.S. Pat. No. 4,376,110; Ausubel et al, eds., supra, Harlow and Lane ANTIBODIES: A LABORATORY MANUAL Cold Spring Harbor Laboratory (1988); and Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mab of the present invention may be cultivated in vitro, in situ or in vivo. Production of high titers of mabs in vivo or in situ makes this the presently preferred method of production.

Chimeric antibodies are molecules different portions of which are derived from different animal species, such as those having the variable region derived from a murine mab and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066–1074 (1986); Robinson et al., International Patent Publication, WO 9702671 (published 7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the Mab with the Mab to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original Mab which induced the anti-Id. Thus, by using antibodies to the idiotypic determinants of a Mab, it is possible to identify other clones expressing antibodies of identical specificity.

Accordingly, Mabs generated against IFNAB-BPI, IFNAB-BPII, and related proteins of the present invention may be used to induce anti-Id antibodies in suitable animals, such as BALB/c mice. Spleen cells from such immunized mice are used to produce anti-Id hybridomas secreting anti-Id Mabs. Further, the anti-Id Mabs can be coupled to a carrier such as keyhole limpet hemocyanin (KLH) and used to immunize additional BALB/c mice. Sera from these mice will contain anti-anti-Id antibodies that have the binding properties of the original Mab specific for an IFNAB-BP epitope.

The anti-Id Mabs thus have their own idiotypic epitopes, or "idiotopes" structurally similar to the epitope being evaluated, such as IFNAB-BPI or IFNAB-BPII.

The term "antibody" is also meant to include both intact molecules as well as active fractions thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of IFNAB-BPI, IFNAB-BPII, and related proteins according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect IFNAB-BPI, IFNAB-BPII or related proteins in a sample or to detect presence of cells which express such proteins of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of IFNAB-BPI, IFNAB-BPII and related proteins of the present invention. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of IFNAB-BPI, IFNAB-BPII or related protein but also its distribution on the examined tissue. Using the present invention, those of ordinary skill will readily perceive that any of wide variety of histological methods (such as staining procedures) can be modified in order to achieve such in situ detection.

Such assays for IFNAB-BPI, IFNAB-BPII or related proteins of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying IFNAB-BPI, IFNAB-BPII or related proteins, and detecting the antibody by any of a number of techniques well-known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon, amylases, natural and modified celluloses, polyacrylamides, agarose, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrrier configuration may be spherical, as in a bead, or cylindrical, as in the inside surface of a test tube, or the external surface of a rod. Alternatively, the surface may be flat such as a sheet, test strip, etc. Preferred supports or carriers include polystyrene beads. Those skilled in the art will know many other suitable carriers for binding antibody or antigen, or will be able to ascertain the same by use of routine experimentation.

The binding activity of a given lot of antibody in accordance with the present invention may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6- phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect IFNAB-BPI or IFNAB-BPII through the use of a radioimmunoassay (RIA). A good description of RIA maybe found in Laboratory Techniques and Bio chemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a γ-counter or a scintillation counter or by autoradiography.

It is also possible to label an antibody in accordance with the present invention with a fluorescent compound. When the fluorescently labeled antibody is exposed to light of the proper wavelength, its presence can be then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriamine pentaacetic acid (ETPA).

The antibody can also be detectably labled by coupling it to biotin. Biotinylated antibody can then be detected by avidin or streptavidin coupled to a fluorescent compound or to an enzyme such as peroxidase or to a radioactive isotope and the like.

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen form the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A "simultaneous" assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The present invention also provides DNA molecules encoding any of the proteins of the present invention as defined above, replicable expression vehicles comprising any such DNA molecules, host cells transformed with any such expression vehicles including prokaryotic and eukaryotic and host cells, preferably monkey COS cells.

The invention also includes a process for the production of any of the proteins of the present invention by culturing a transformed cell in accordance with the present invention and recovering the protein encoded by the DNA molecule and the expression vehicle within such transformed host cell.

The invention will now be illustrated by the following nonlimiting examples:

EXAMPLE 1

Protein Sequence Analysis of IFNAB-BP

Pure IFNAB-BP, obtained as described in grandparent application Ser. No. 08/115,741 now abandoned was adsorbed on a PVDF membrane (Pro-Spin, Applied Biosystems, USA) and the membrane was subjected to protein sequence analysis on a Model 475 microsequencer (Applied Biosystems, USA). The following major sequence was obtained:

Asp-Ser-Pro-Asp-Tyr-Thr-Asp-Glu-Ser-Arg-Thr-Phe-Lys-Ile-Arg-Leu-Arg (SEQ ID NO:9)

In addition, a secondary polypeptide having three additional amino acid residues (Ile-xxx-Tyr) at the N-terminus of the major sequence was detected (xxx denotes an unidentified amino acid). The resulting sequence is completely different from that of the already known IFN-AB receptor (INFAR, reference 14) and is different from any other known protein. It is different from any other known protein. It is also different from any protein coded by a known DNA sequence, as determined by searching Swissprot and Genebank databases by the program FastA (33). Hence this protein is a novel IFN-α binding protein. Upon isolation of cDNA clones (see below), it was clarified that residue 10 is Cys and not Arg and residue 15 is Ser and not Arg. Furthermore, xxx was identified as Ser. It is known that Cys cannot be identified by the protein microsequencer, while sometimes Ser is destroyed in the analytical process and therefore it is not identified.

A sample of the urinary IFNAB-BPI was digested with CNBr, resolved on SDS-PAGE and blotted onto a PVDF membrane. Seven discrete peptide bands, designated cb1–cb7 were resolved and detected on the membrane upon staining with Coomassie blue. Each band was excised and subjected to protein microsequencing. One of the peptides, cb7, was smaller than 10,000 and gave the following internal sequence (Met precedes the actual sequence):

Met-Val-Lys-Phe-Pro-Ser-Ile-Val-Glu-Glu-Glu-Leu-Gln-Phe-Asp-Leu-Ser-Leu-Val-Ile-Glu-Glu-Gln-Ser-Glu-Gly-Ile . . . (residues 151–177 of SEQ ID NO:2)

Another peptide, cb3, had the following sequence (Met precedes the actual sequence):

Met-Ser-Lys-Pro-Glu-Asp-Leu-Lys-Val-Val-Lys-Asn-XXX-Ala-Asn-Thr-Thr-Arg . . . (SEQ ID NO:10)

Residue 13 was later identified as Cys, as determined from the cDNA sequence (see below). Cys residues cannot be identified by protein microsequencing.

Another peptide, cb6, had the following sequence (Met precedes the actual sequence):

Met-Ser-Gly-XXX-Phe-Thr-Tyr-Ile-Ile-Asp-Lys-Leu-Ile-Pro-Asn-Thr-Asn-Tyr . . . (SEQ ID NO:11)

Residue 4 was later identified as Asn, as determined from the cDNA sequence (see below). This Asn residue is part of a potential glycosylation signal sequence (Asn-Phe-Thr) and the absence of Asn signal in the protein sequence indicates that it is indeed glycosylated.

The other peptide bands were identified by sequencing as products of incomplete digestion with CNBr. They gave either the N-terminal domain as previously found for IFNAB-BP or the same internal sequences of cb3, cb6 or cb7.

EXAMPLE 2

Protein Sequence Analysis of the C-terminal Peptide of Urinary IFNAB-BP

A sample of urinary IFNAB-BP (≈10 μg) was reduced by DTT, alkylated by iodoacetamide and digested with endoproteinase Lys C (Boehringer Mannheim, Germany) at a 1:50 enzyme to substrate ratio. The resulting peptide mixture was resolved by RP-HPLC, on an RP18 column (Aquapore RP18, Applied Biosystems Inc.) using a gradient of acetonitrile in aq. 0.1% trifluoroacetic acid. Individual peptide peaks were covalently attached to Sequalon AA membranes (Millipore, Bedford Mass.) and subjected to N-terminal sequencing as above. One of the peptides was identified as the C-terminal peptide having the following sequence:

Cys-Thr-Leu-Leu-Pro-Pro-Gly-Gln-Glu-Ser-Glu-Phe-Ser (SEQ ID NO:12)

The C-terminal sequence corresponded to that of the 4.5 kb cDNA clone (see below) and could be distinguished from that of the putative protein coded by the 1.5 kb cDNA by the last two amino acid residues (Phe12-Ser13 instead of Ser-Ala). Hence the soluble receptor isolated from urine is identified as IFNAB-BPII. It is translated independently from a specific 4.5 kb mRNA and is not formed by shedding of the cell-surface receptor.

EXAMPLE 3

Construction of Degenerate Sense and Antisense Primers and Identification of a Non-degenerate Sequence of IFNAB-BP cDNA.

The sequence of peptide cb7 was reverse-translated into sense (amino acids 1–8) and antisense (amino acids 27–20) primers. Decanucleotides and nonanucleotides, containing the BamH I and Sal I endonuclease restriction sequences, respectively, were added to the 5' ends of the primer oligonucleotides (FIG. 1A). Total RNA was extracted from Daudi and WISH cells and first strand cDNA was generated with reverse transcriptase, using either the antisense oligonucleotide mixture or oligo d(T) as a primer. The resulting cDNA fragment was then amplified in a polymerase chain reaction (PCR), using the combined sense and antisense degenerate primers. Analysis of the PCR products on a 3t agarose gel showed the expected 101 bp band, obtained with the cDNA of both Daudi and WISH cells (FIG. 1B). The 101 bp fragment was restricted with BamH I and Sal I, cloned into pBluescript II KS+ (Stratagene) and 5 clones were sequenced. The sequence of the region flanked by the sense and antisense primers was invariant and encoded the expected sequence of amino acid residues 9–19 of peptide cb7 (FIG. 1C). A 35 bp oligonucleotide, corresponding to the non-degenerate internal sequence was then synthesized and used for screening of cDNA libraries.

EXAMPLE 4

Identification of Partial cDNA Clones of IFNAB-BPI

The synthetic 35 bp non-degenerate oligonucleotide of Example 3 was [$^{32}$P] labeled and used for screening of a lambda gt11 cDNA library of human HeLa cells (Clontech). Five positive clones were identified. One of these clones, named q10, contained an insert of 1.4 kb. Sequencing of clone q10 yielded a sequence having an open reading frame, in which a signal peptide, an extracellular domain, a transmembrane domain and part of the intracellular domain were identified (FIG. 2). DNA sequences coding for the N-terminal protein sequence, as well as the sequences of the three CNBr peptides cb3, cb6 and cb7 of the urinary IFNAB-BP were identified within the extracellular domain coded by the DNA of clone q10. Some Cys and Ser residues (dot underlined, FIG. 2) were not correctly identified by the protein sequencing. However, it is known that the method used for protein sequencing does not call Cys residues and occasionally it misses Ser residues. Also an Asn residue in peptide cb6 was not detected, indicating that it is glycosylated. Comparison of the DNA sequence of clone q10 with Genebank database did not show any identity to any known sequence. Hence this clone contains a new DNA sequence.

EXAMPLE 5

Northern Blotting of Human mRNA

Figure 3:
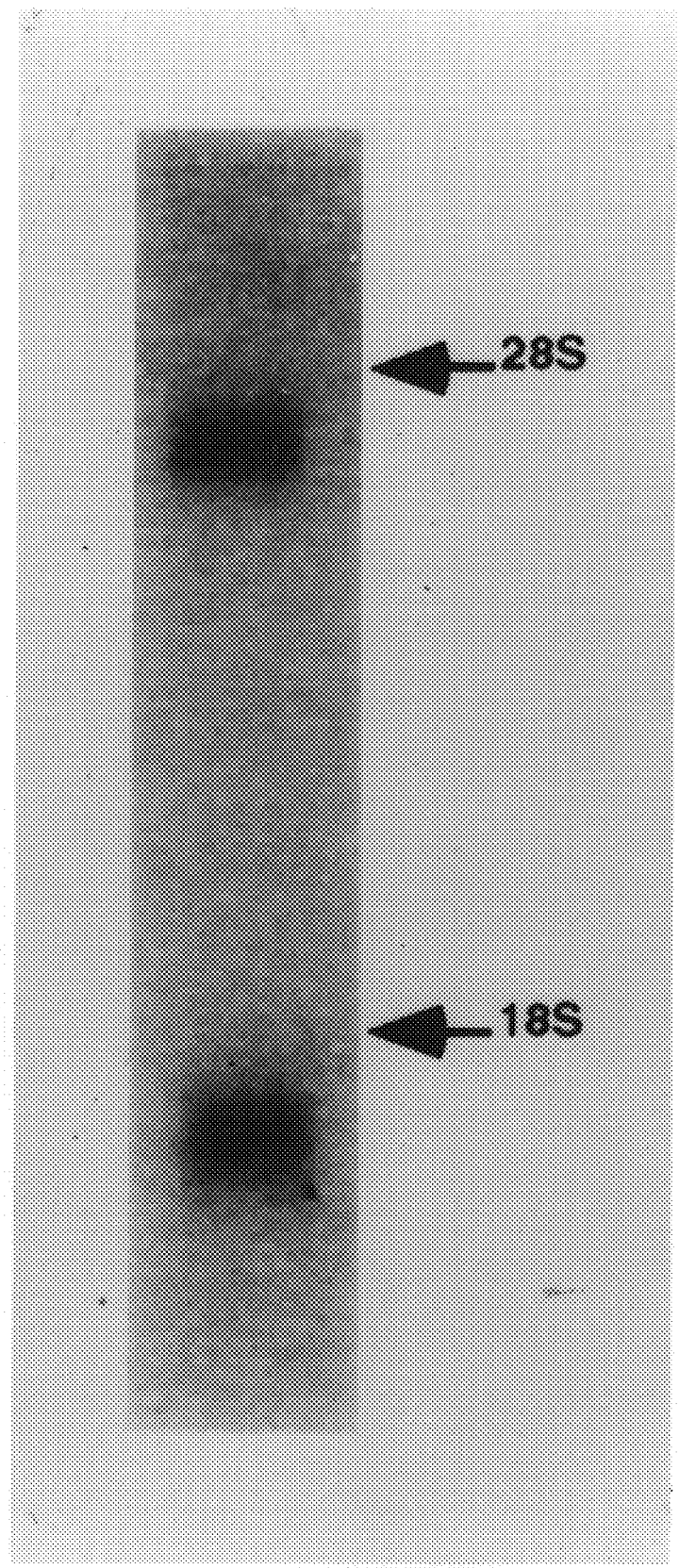
FIG. 3 shows detection of mRNA by Northern blotting with a specific probe, common to the sequence of IFNAB-BPI and IFNAB-BPII.

A radiolabelled DNA probe was prepared from clone q10 and used for Northern blot hybridization of poly A+ mRNA from two human cell lines: Daudi and WISH. In both cases two specific bands were observed, one, corresponding to 1.5 kb and another one, corresponding to 4.5 kb. Based on the intensity of the bands it was estimated that the 1.5 kb mRNA is about twice as abundant as the 4.5 kb mRNA. The signal obtained with the RNA from WISH cells was barely seen, while the signal of RNA from Daudi cells (FIG. 3) was detectable. The 1.5 kb mRNA is translated into a precursor of IFNAB-BPI which is a cell surface interferon receptor. The longer mRNA represents a different transcript, coding for a different protein that shares at least about 100 amino acid residues with IFNAB-BPI. This protein is the precursor of IFNAB-BPII, later shown to be a soluble form of the interferon-α/β receptor.

EXAMPLE 6

Identification of Complete cDNA Clones of IFNAB-BPI and IFNAB-BPII

A human monocyte cDNA library, constructed in phage γpCEV9 (Gutkind, J. S., et al., Molec. Cell. Biol. 11, 1500–1507, 1991), was then screened with a 397 bp probe made by PCR from the coding region of clone q10. We isolated 22 clones with a 1.5 kb insert and two clones with a 4.5 kb insert from $10^6$ independent phages. DNA sequence analysis of two 1.5 kb clones (γpCEV9-m6 and γpCEV9-m24), as well as the entire open reading frame of the two 4.5 kb clones (γpCEV9-m19 and γpCEV9-m27) was performed. The 1.5 kb clones coded for a complete precursor of IFNAB-BPI, which is a cell surface receptor, with an open reading frame of 331 codons (FIG. 4). The protein and CNBr peptide sequences, obtained from urinary IFNAB-BP (dot underlined, FIG. 4), were all identified within the translated DNA sequence. Partial sequencing of the two 4.5 kb clones revealed the same 5' sequence of 237 codons as present in the 1.5 kb clones, followed by a different sequence that included a termination signal after codon 239 (FIG. 5). Altogether, the following codons were different between the IFNA-BPII sequence of FIG. 5 and the sequence of clone q10 shown in FIG. 2: codon 10 (Val instead of Phe0; codon 13 (Leu instead of His); codon 108 (Thr instead of Ile) and codons 238–240 (Phe-Ser-Stop instead of Ser-Ala-Glu). No open reading frame was seen beyond the stop codon in any of the three reading frames in both of the 4.5 kb clones. Hence the 4.5 kb which is IFNAB-BPII, identical in its C-terminal sequence to the one isolated from urine. The two mRNAs coding for the precursor proteins of both IFNAB-BPI and IFNAB-BPII are derived from the same gene, probably by alternative splicing.

EXAMPLE 7

Construction of a Mammalian Expression Vector and Production of Recombinant IFNAB-BPI and IFNB-BPII A DNA coding for the signal sequence and the extracellular domain of IFNAB-BPI corresponds, was generated by PCR with VENT DNA polymerase (Stratagene), using synthetic sense and antisense primers, carrying Xba I restriction sites (FIG. 6A) and using q10 DNA as a template. The resulting PCR product (FIG. 6B) was restricted by Xba I and ligated into the expression vector pEF-BOS to yield pEF-BOS-sABR (FIG. 6C, reference 46). The construct was confirmed by DNA sequencing. Competent E. coli were transformed and clones having the IFNAB-BPI sequence in a correct orientation were isolated. The PEF-BOS-sABR construct was used for transfection of monkey COS cells. These cells expressed 12 ng/ml of recombinant soluable IFNAB-BPI that was obtained in the cell culture supernatant, as determined by ELISA and by its ability to inhibit the biological (antiviral) activity of human interferons alpha and beta. In analagy, the DNA region coding for IFNAB-BPII in the 4.5 kb clone is inserted into a mammalian expression vector as described for the extracellular domain of IFNAB-BPI and used for transforming cells. Such cells are producing active IFNAB-BPII that is secreted to the culture medium of said cells.

EXAMPLE 8

Construction of Eukaryotic Expression Vectors and Expression of IFNAB-BPI and IFNAR in Murine Cells A DNA coding for the entire of IFNAB-BPI was generated by PCR with VENT DNA polymerase (Stratagene), using synthetic sense and antisense primers, carrying Xba I restriction sites and using plasmid pCEV9-m6 as a template. The resulting PCR product was restricted by Xba I and ligated into the expression vector pEF-BOS to yield pEF-BOS-IFNABR. The cDNA corresponding to IFNAR (14) was generated by RT-PCR (48), using specific oligonucleotides. The amplified product was cloned into the Xba I restriction site of the PEF-BOS expression vector (46), to yield pEF-BOS-IFNAR. These construct were confirmed by DNA sequencing. Competent E. coli were transformed and clones having the IFNAB-BPI and INFAR sequences in a correct orientation were isolated.

Murine cells expressing the cloned IFNAB-BPI cDNA in a stable manner were developed. Exponentially growing NIH-3T3 cells ($1.5 \times 10^6$ in 10 cm plates) were contransfected by the calcium phosphate precipitation method (49) with pSv2neo (2 μg), together with pEF-BOS-IFNABR (10 μg DNA). Independent G418-resistant colonies were identified and sub-cloned. Clones expressing high levels of IFNAB-BPI were identified by binding of an antibody directed against the urinary IFNAB-BPI and by binding of $^{125}$I-IFN-α2 (Table IV).

For binding of anti IFNAB-BPII antibodies, cells ($1 \times 10^6$) were seeded in 35 mm wells (6 well plates, Costar) and grown to confluency (20 hr). The cells were washed with DMEM containing 2% FBS and 0.1%. sodium azide (Wash medium) followed by an incubation of 20 min. with the Wash medium. Rabbit anti IFNAB-BPII antibodies (2 ml, 1:500 in the Wash medium) were added to the washed wells and the cells were incubated for 2h at room temperature. The cells were washed 3 times, $^{125}$I-protein A (2 ml, 250,000 cpm in the Wash medium) was added and the cells were further incubated for 45 min. The cells were washed 3 times, harvested with trypsin and counted.

For binding of $^{125}$I-IFN-α2, cells ($1 \times 10^6$) were seeded in 35 mm wells (6 well plates, Costar) and grown to confluency (20 hr). The cells were washed with DMEM containing 2% FBS and 0.1% sodium azide (Wash medium) followed by an incubation of 20 min. with the Wash medium. $^{125}$I-IFN-α2 ($2-3 \times 10^5$ cpm, $10^8$ units/mg, $5 \times 10^7$ cpm/μg) was added and incubation continued for 2 hr at room temperature. The cells were washed 3 times, harvested with trypsin and counted.

SDS-PAGE under non-reducing conditions of a detergent extracts of positive clones (e.g., Clone 369.11), followed by immunoblotting with the above mentioned antibody gave a strong band of about 51 kDa (FIG. 7).

Murine cells expressing IFNAR were similarly developed by transfection with plasmid pEF-BOS-IFNAR. Clone No. 470.6 was IFNAR-positive, as determined by the ability of huIFN-αB to effectively induce an antiviral response in these cells. As expected, other type I IFNs (e.g., huIFN-β) were not active in Clone 470.6.

Clones 369.11 and 470.6, expressing IFNAB-BPI and IFNAR, were then transfected with the complementary receptor protein (pEF-BOS-IFNAR and pEF-BOS-IFNABR, respectively). For stable coexpression, G418-resistant clones, expressing either IFNAR or IFNAB-BPI were transfected with pSV2hygro (2 μg), together with either pEF-BOS-IFNABR or pEF-BOS-IFNAR as above. Hygromycin and G418-resistant clones, co-expressing both IFNAR and IFNAB-BPI were isolated and sub-cloned. IFNAR-positive clones, derived from Clone 369.11, were identified by their antiviral response to huIFN-αB, while IFNAB-BPI-positive clones, derived from Clone 470.6, were identified by binding of both anti IFNAB-BPII antibodies and $^{125}$I-IFN-α2. Clone 508.12, derived from Clone 369.11, and Clone 1306, derived from Clone 470.6, bound both $^{125}$-IFN-α2 and IFN-α/βR antibody (Table IV). In addition, they responded to huIFN-aB in an antiviral assay. Hence we concluded that these clones express both IFNAB-BPI and a functional IFNAR.

TABLE IV

Expression of IFNAB-BPI in various cells.

| Cells | Bound IFNAB-BPII antibody (cpm) | Bound $^{125}$I-IFN-α2 (cpm) |
|---|---|---|
| 470.6 (IFNAR) | 236 | 90 |
| 369.11 (IFNAB-BPI) | 4243 | 12,500 |
| 508.12 (IFNAB-BPI & IFNAR)[a] | 7728 | 70,240 |
| 1306 (IFNAR & IFNAB-BPI)[b] | 3369 | 32,000 |

[a]Derived from Clone 369.11
[b]Derived from Clone 470.6

EXAMPLE 9

Determination of the Affinity of IFNAB-BPI and IFNAR Expressed in Murine Cells

Clones expressing either IFNAR or IFNAB-BPI were tested for binding of $^{125}$I-huIFN-α2 and the binding data were evaluated by a Scatchard analysis. Cells (1×10$^6$) were seeded in 35 mm wells (6 well plates, Costar) and grown to confluency (20 h). The cells were washed with DMEM containing 2% FBS and 0.1% sodium azide (Wash medium) followed by an incubation of 20 min. with the same medium. $^{125}$I-IFN-α2 (2–3×10$^5$ cpm, 10$^8$ units/mg, 5×10$^7$ cpm/μg) was added, together with the indicated concentrations of non-labeled IFN-α2 and incubation continued for 2 hr at room temperature. The cells were washed 3 times with the Wash Medium, harvested with trypsin and counted. Binding data was analyzed by the LIGAND program (50).

Cells expressing IFNAR only (Clone 470.6) did not exhibit any specific binding of $^{125}$I-IFN-α2 (FIG. 8 A) and hence, no Kd value of such putative binding sites could be derived. In contrast with Clone 470.6, high affinity, specific and saturable binding was obtained with cells expressing IFNAB-BPI alone (Clone 369.11). The Kd of this binding was $3.6 \times 10^{-9}$ M at 23° C. (Table V).

Binding of $^{125}$I-IFN-α2 to 508.12 cells (expressing both IFNAB-BBPI and IFNAR) was evaluated by a Scatchard analysis and the results were compared with those of Clone 369.11 (expressing only IFNAB-BPI). Upon co-expression of IFNAB-BPI and IFNAR, a saturable binding was obtained and the affinity for IFN-α2 increased by about 10 fold (FIG. 8), approaching that of the receptor in Daudi cells (Kd=$4.0 \times 10^{-10}$ M vs. $1.6 \times 10^{-10}$ M, respectively, Table V). This result indicates that IFNAR and IFNAB-BPI cooperate in ligand binding.

TABLE V

Binding characteristics of various host cells (ligand = $^{125}$I-IFN-α2).

| Cell (receptor) | binding sites Per cell | Kd (M) at 20° C. |
|---|---|---|
| human Daudi | 4900 11% | $1.6 \times 10^{-10}$ |
| 470.6 (IFNAR) | 0 | (–) |
| 369.11 (IFNAB-BPI) | 80,000 11% | $3.6 \times 10^{-9}$ |
| 508.12 (IFNAB-BPI & IFNAR) | 59,000 10% | $4.07 \times 10^{-10}$ |

EXAMPLE 10

Determination of the Affinity of Urinary IFNAB-BPII

Human IFN-α2 was immobilized on a sensor chip of BIAcore (Pharmacia, Sweden) by an automatic procedure provided by the manufacturer. About 30 fmol of IFN-a2 were immobilized. Urinary IFNAB-BPII diluted in phosphate-buffered saline (PBS) to several concentrations (28–112 nM) was passed through the sensogram chip and the extent of association and dissociation (in PBS) was recorded. Based on the resulting data a Kd value of $3.12 \times 10^{-9}$ M was calculated (FIG. 9). Thus the affinity of urinary IFNAB-BPII is very similar to that of IFNAB-BPI expressed in host cells.

EXAMPLE 11

Expression of IFNAB-BPI and IFNAB-BPII in E. Coli, Yeast and Insect Cells

IFNAB-BPI and IFNAB-BPII are also produced by additional recombinant cells such as prokaryotic cells, e.g., E. coli, or other eukaryotic cells, such as yeast and insect cells. Well known methods are available for constructing appropriate vectors, carrying DNA that codes for either IFNAB-BPI or IFNAB-BPII and their active fractions suitable for transforming E. coli and yeast cells, or infecting insect cells in order to produce recombinant IFNAB-BPI and IFNAB-BPII. For expression in yeast cells, the DNA coding for IFNAB-BPI or IFNAB-BPII (Examples 5 and 6) is cut out and inserted into expression vectors suitable for transfection of yeast cells. For expression in insect cells, the DNA coding for IFNAB-BPI or IFNAB-BPII is inserted into baculovirus and the insect cells are infected with said recombinant baculovirus. For expression in E. coli the DNA coding for either IFNAB-BPI or IFNAB-BPII is subjected to site directed mutagenesis with appropriate oligo-nucleotides, so that an initiation ATG codon is inserted just prior to the first codon of mature IFNAB-BPI (FIG. 2) or IFNAB-BPII. Alternatively, such DNA can be prepared by PCR with suitable sense and antisense primers. The resulting cDNA constructs are than inserted into appropriately constructed prokaryotic expression vectors by techniques well known in the art (35).

EXAMPLE 12

Construction of Recombinant Fusion Proteins of IFNAB-BPI and IFNAB-BPII

The production of proteins comprising either the ligand-binding domain of IFNAB-BPI or IFNAB-BPII, fused to the constant region of IgG1 heavy chain may be carried out as follows: the DNA of IFNAB-BPI or IFNAB-BPII is subjected to site-directed mutagenesis with appropriate oligo-nucleotides so that a unique restriction site is introduced immediately before and after sequences coding to the ligand binding extracellualr domains. Alternatively, such DNA may be prepared by PCR with specifically designed primers bearing the restriction sites. Another plasmid bearing the constant region of IgG1 heavy chain, e.g. pRKC042Fc1 (47) is subjected to similar site-directed mutagenesis to introduce the same unique restriction site as close as possible to Asp 216 of IgG1 heavy chain in a way that allows translation in phase of the fused protein. A dsDNA fragment, consisting of 5' non-translated sequences and encoding for either IFNAB-BPII or the ligand-binding domain of IFNAB-BPI is prepared by digestion at the unique restriction sites. The mutated pRKCD42Fc1 is similarly digested to generate a large fragment containing the plasmid and the IgG1 sequences. The two fragments are then ligated to generate a new plasmid, encoding a polypeptide precursor consisting of either IFNAB-BPII or the ligand-binding domain of INFAB-BPI and about 227 C-terminal amino acids of IgG1 heavy chain (hinge region and CH2 and CH3 domains). The DNA encoding the fused proteins may be isolated from the plasmid by digestion with appropriate restriction enzymes and then inserted into efficient prokaryotic or eukaryotic expression vectors.

EXAMPLE 13

Construction of Recombinant Fusion Proteins of IFNAB-BPI and IFNAB-BPII Together with INFAR The production of proteins comprising either the extracellular domain of IFNAB-BPI or IFNAB-BPII, fused to the constant region of IgG1 heavy chain may be carried out as described in example 12. The production of a protein comprising the extracellular domain of IFNAR, fused to the constant region of IgG1 light chain is similarly carried out. Eukaryotic expression vectors coding for either the ligand-binding domain of IFNAB-BPI fused to the constant region of IgG1 heavy chain or IFNAB-BPII, fused to the constant region of IgG1 heavy chain are used for co-transfection of suitable mammalian host cells together with a eukaryotic expression vector coding for the extracellular domain of IFNAR, fused to the constant region of IgG1 light chain. Positive transfectants will secrete a composite protein consisting of the IgG1 constant regions, the extracellular domain of IFNAR replacing the variable regions of IgG1 light chains and either IFNAB-BPII or the ligand-binding domain of IFNAB-BPI replacing the variable regions of IgG1 heavy chains.

In another example the constant regions of the heavy and light chains are switched, namely the extracellular domain of IFNAR is fused to the constant regions of IgG2 heavy chain while either the ligand-binding domain of IFNAB-BPI or IFNAB-BPII are fused to the constant regions of IgG2 light chain.

Based on example 9, these fused proteins are expected to exhibit about 10-fold higher affinity for IFN-A as compared with that of IFNAB-BPI or IFNAB-BPII.

EXAMPLE 14

Preparation of Polyclonal Antibodies to IFNAB-BP

Rabbits were initially injected subcutaneously with 5 $\mu$g of a pure preparation of the urinary IFNAB-BP emulsified in complete Freund's adjuvant. Three weeks later they were injected again subcutaneously with 5 $\mu$g of the preparation in incomplete Freund's adjuvant. Four additional injections as solution in PBS were given at 10 day intervals. The rabbits were bled 10 days after the last immunization. The development of antibody level was followed by a solid-phase radio-immunoassay (sRIA), using 96-well PVC plates coated overnight at 4° C. with IFNAB-BP (1 $\mu$g/ml), in phosphate-buffered saline (PBS). The plates were then blocked with bovine serum albumin (BSA, 0.5%), Tween 20 (Sigma USA, 0.05%) in PBS overnight at 4° C. The plates were reacted with 5 fold dilutions of the rabbit antiserum for 4 hours at room temperature, washed and reacted with $^{125}$I-protein A ($10^5$ cpm/well) in PBS for 45 min. at room temperature. The plates were then washed; individual wells were cut and counted. The titer is calculated as the reciprocal of the maximal dilution that gave counts 10 fold higher than control antiserum. The titer after 5 injections was greater than 1:60,000.

The development of antibody level was also followed by the ability of the antiserum to block the antiviral activity of human IFN-α2. Preformed monolayers of human WISH cells in 96-well plates were incubated with two-fold dilutions of the antiserum, starting at a dilution of 1:250 in well no. 1, for 1 hour at 37° C. IFN-α2 (10 u/ml, final) was then added and after 1 hour at 37° C., the cells were challenged with vesicular stomatitis virus. The neutralizing titer after 7 immunizations was 120,000 antiviral $\mu$/ml.

EXAMPLE 15

Preparation of Monoclonal Antibodies to IFNAB-BP

Female Balb/C mice (3 months old) were first injected with 2 $\mu$g purified IFNAB-BP in an emulsion of complete Freund's adjuvant, and three weeks later, subcutaneously in incomplete Freund's adjuvant. Three additional injections were given at 10 day intervals, subcutaneously in PBS. A binding titer of 1:60,000 was obtained by sRIA (see Example 9). Final boosts were given intraperitoneally 4 and 3 days before the fusion to the mouse showing the highest binding titer. Fusion was performed using NSO/1 myeloma cell line and lymphocytes prepared from both the spleen and lymph nodes of the animal as fusion partners. The fused cells were distributed into microculture plates and the hybridomas were selected in DMEM supplemented with HAT and 15% horse serum. Hybridomas that were found to produce antibodies to IFNAB-BP were subcloned by the limiting dilution method and injected into Balb/C mice that had been primed with pristane for the production of ascites. The isotypes of the antibodies were defined With the use of a commercially available ELISA kit (Amersham, U.K.).

The screening of hybridomas producing anti-IFNAB-BP monoclonal antibodies was performed as follows: Hybridoma supernatants were tested for the presence of anti-IFNAB-BP antibodies by an inverted solid phase radioimmunoassay (IRIA). PVC microtiter plates (Dynatech Laboratories, Alexandria, Va.) were coated with affinity purified goat anti-mouse serum F(ab)$_2$ antibodies (Jackson Labs, USA) (10 $\mu$g/ml, 100 $\mu$l/well). Following overnight incubation at 4° C. the plates were washed twice with PBS containing BSA (0.5%) and Tween 20 (0.05%) and blocked in washing solution for at least 2 hrs at 37° C. Hybridoma culture supernatants (100 $\mu$l/well) were added and the plates were incubated for 4 hrs at 37° C. The plates were then washed three times with the washing solution and $^{125}$I-IFNAB-BP (100 $\mu$l, $10^5$ cpm) was added for further incubation of 16 hrs at 4° C. The plates were washed 3 times and individual wells were cut and counted in a gamma counter. Samples giving counts that were at least 5 times higher than the negative control value were considered positive (Table VI). Five positive clones were selected, subcloned for further studies and characterized. All clones were of IgG$_1$ isotype.

TABLE VI

Clones producing monoclonal antibodies to IFNAB-BP

| Clone No. | Dilution | iRIA - CPM |
| --- | --- | --- |
| 2.1 | 1:1 | 2140 |
| 5.73 | 1:1 | 3292 |
| 30.24 | 1:1 | 5548 |
| 46.10 | 1:1000 | 29,818 |
| 70.6 | 1:1 | 1214 |
| Control antibody | 1:1 | 20 |

EXAMPLE 16

Affinity Chromatography of IFNAB-BP with Monoclonal Antibodies

Antibodies against IFNAB-BP were utilized for the purification of IFNAB-BP by affinity chromatography. The monoclonal antibody No. 5.73 was used in this example for affinity chromatography. Ascitic fluid containing the monoclonal antibody secreted by hybridoma No. 5.73 was purified by ammonium sulfate precipitation at 50% saturation followed by extensive dialysis against PBS. About 10mg of immunoglobulins were bound to 1 ml Affigel 10 (BioRad USA), as specified by the manufacturer.

250 ml of human urinary proteins (equivalent to 250 l of crude urine) were loaded on 0.5 ml of the anti IFNAB-BP antibody column at 4° C. at a flow rate of 0.25 ml/min. The column was washed with PBS until no protein was detected in the washings. IFNAB-BP was eluted by 25 mM citric acid buffer, pH 2.2 (8×1 column volume fractions) and immediately neutralized by 1 M $Na_2CO_3$. Silver stain analysis of SDS PAGE of the eluted fractions reveals a major band of M.W. of 40,000. Further purification of this preparation was obtained by size exclusion chromatography.

EXAMPLE 17

ELISA test of IFNAB-BPII

Microtiter plates (Dynatech or Maxisorb, by Nunc) were coated with anti-IFNAB-BP monoclonal antibody No. 46.10 (Ig fraction, 120 μl/well, 10 μg/ml in PBS) overnight at 4° C. The plates were washed with PBS containing BSA (0.5%) and Tween 20 (0.05%) and $NaN_3$ (0.02%) (blocking solution) and blocked in the same solution over night at 37° C. The tested samples were serially diluted twofold (starting with 1:4) in the blocking solution containing 0.1% NP40 and 0.65 M naCl and added to the wells (100 μl/well) for 4 hrs at 37° C. The plates were then washed 3 times with PBS containing 0.05% Tween 20 (PBS/Tween) followed by the addition of rabbit anti-IFNAB-BPII serum (1:1000 in Blocking solution but without $NaN_3$, 100 μl/well) for further incubation overnight at 4° C. The plates were washed 3 times with PBS/Tween, (100 Tween 20 (0.05%) μl/well), and a conjugate of goat-anti-rabbit horseradish peroxidase (HRP, Jackson Labs, 1:10,000 in PBS/Tween, 100 μl/well) was added for 2 hrs at room temperature. The plates were washed 3 times with PBS/Tween and the color was developed adding to each well 100 μl of a freshly prepared solutions of ABTS (2,2'-azino-bis (3-ethylbenzthiazoline-6-sulfonic acid, Sigma, 10 mg; 6.4 ml $H_2O$; 2.2 ml of 0.2M $Na_2HPO_4$; 1.4 ml 0.2 M citric acid; 1 μl $H_2O_2$) as a substrate. The color develops by 30 min. and the reaction may be stopped by addition of 100 μl/well of 0.2 M citric acid. The plates were read by an automatic ELISA reader at 405 nm, correcting for non-specific reading at 630 nm. The lower limit of detection of this assay was 30 pg/ml (FIG. 10).

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation.

References

1. Taylor, J. L. and Grossberg, S. E. (1990). Recent progress in interferon research: molecular mechanisms of regulation, action and virus circumvention. Virus Research 15:1–26.
2. Bisceglie A. M., Martin, P., Kassianides C., Lisker-Melman, M., Murray, L., Waggoner, J., Goodmann, Z., Banks, M. S. and Hoofnagle, J. H. (1989). Recombinant interferon alpha therapy for chronic hepatitis C. A randomized, double-bind, placebo-controlled trial. New Eng. J. Med. 321:1506–1510.
3. McDonnell, W. M. and Elta G. H. (1992). Acute hepatitis C infection: interferon finally succeeds. Gastroenterology (US) 103:1359–1360.
4. Friedman-Kien, A. E., Eron, L. J., Conant, M., Growdon, W., Badiak, H., Bradstreet, P. W., Fedorczyk, D., Trout, R. and Plesse, T. F. (1988). Natural interferon alpha for treatment of condylomata acuminata. J. Am. Med. Assn., 259: 533–538.
5. Mains, J. and Handley, J. (1992). Interferon: current and future clinical uses in infectious disease practice. Int. J. Stud. AIDS 3:4–9.
6. Berman, E., Heller, G., Kempin, S., Gee, T., Tran, L. and Clarkson, B. (1990). Incidence of response and long term follow up in patients with hairy cell leukemia treated with recombinant interferon Alpha-2a, Blood 75: 839–845.
7. Talpaz M., Kantarjian, H. M., McCredie, K. B., Keating, M. J., Trujillo, J. and Gutterman, J. (1987), Clinical investigation of human alpha interferon in chronic myelogenous leukemia. Blood 69:1280–1288.
8. De Wit, Schattenkerk, J. K. M. E., Boucher, C. A. B., Bakker, P. J. M., Veenhof, K. H. N. and Danner, S. A. (1988). Clinical and virological effects of high-dose recombinant-interferon-a in disseminated AIDS-related Kaposi's sarcoma. Lancet 2: 1214–1222.
9. Klippel, J. H., Carrete, S., Preble, D. T., Friedman, R. M. and Grimley P. M. (1985). Serum alpha interferon and lymphocyte inclusions in systemic lupus erythematosus. Annals of the Rheumatic Diseases 44:104–108.
10. Lau, A. S., Der, S. D., Read, S. E., and Williams, B. R. (1991). Regulation of tumor necrosis factor receptor expression by acid-labile interferon-alpha from AIDS sera. AIDS Res. Hum. Retroviruses 7:545–552.
11. Stewart, T. A. (1993). Induction of type I diabetes by interferon-a in transgenic mice. Science 260:1942–1946.
12. Tsavaris, N., Mylonakis, N., Bacoyiannis, C., Tsoutsos, H., Karabelis,A., and Kosmidis, P. (1993). Treatment of renal cell carcinoma with escalating doses of alphainterferon. Chemotherapy (Switzerland) 39:361–366.
13. Branka, A. A. and Baglioni, C. (1981). Evidence that types I and II interferons have different receptors. Nature 294:768–770.
14. Uze G., Lutfalla, G. and Gresser, I. (1990). Genetic transfer of a functional human interferon a receptor into mouse cells: cloning and expression of its cDNA. Cell 60: 225–234.
15. Colamonici, O. R. et al. (1990). Characterization of three monoclonal antibodies that recognize the interferon-a2 receptor. Proc. Natl. Acad. Sci. USA 87:7230–7234.
16. Platanias, L. C. et al. (1992). Expression of the IFN-a receptor in hairy cell leukemia, Brit. J. Haematolog y 82:541–546.
17. Colaminici, O. R. et al. (1993). Identification of a novel subunit of the type I Interferon receptor localized to human chromosome 21. J. Biol. Chem. 268:10895–10899.
18. Benoit, P. et al. (1993). A monoclonal antibody to recombinant human IFN-a receptor inhibits biologic activity of several species of human IFN-a, IFN-b and IFN-omega. J. Immunol. 150:707–716.
19. Novick, D., Engelmann, H., Wallach, D. and Rubinstein, M. (1989). Soluble cytokine receptors are present in normal human urine. J. Exp. Med. 170: 1409–1414.

20. Novick D., Engelmann H., Wallach D., Leitner O., Revel, M. and Rubinstein, M. (1990). Purification of soluble cytokine-receptors from normal human urine by ligand-affinity and immuno-affinity chromatography. J. Chromatography 510: 331–337.
21. Novick D., Engelmann, H., Revel M., Leitner, O. and Rubinstein M. (1991). Monoclonal antibodies to the soluble IL-6 receptor: affinity purification, ELISA, and inhibition of ligand binding. Hybridoma 10:137–146.
22. Engelmann H., Novick, D. and Wallach D. (1990). Two tumor-necrosis-factor binding proteins purified from human urine. Evidence for immunological cross reactivity with cell surface tumor-necrosis-factor receptors. J. Biol. Chem. 265: 1531–1536.
23. Engelmann, H., Aderka, D., Rubinstein, M., Rotman, D. and Wallach, D., (1989). A tumor necrosis factor-binding protein purified to homogeneity from human urine protects cells from tumor necrosis factor toxicity. J. Biol. Chem. 264:11974–11980.
24. Seckinger, P., Isaaz, S. and Dayer, J. M. (1988) A human inhibitor of tumor necrosis factor alpha. J. Exp. Med. 167:1511–1516.
25. Maliszewski, C. R. and Fanslow, W. C. (1990). Soluble receptors for IL-1 and IL-4. Biologicalactivity and therapeutic potential.Trends in Biotechnol. 8:324–329.
26. Eastgate, J. A., Symons, J. A. and Duff G. W. (1990). Identification of an interleukin-l beta binding protein in human plasma. FEBS Letters 260:213–216.
27. Fanslow, F. W., Sims, J. E., Sasenfeld, H., Morrisey, P. J., Gillis, S., Dower, S. K. and Widmer, M. B. (1990). Regulation of alloreactivity in vivo by soluble form of the interleukin-l receptor. Science 248:739–742.
28. Mosley, B., Beckman, M. P., March, C., J., Idzerda, R. L., Gimpel, S., D., VandenBos, T., Friend, D., Alpert, A., Anderson, D., Jackson, J., Wignall, J. M. Smith C., Gallis, B., Sims, J. E., Urdal, D., Widmer, M. B., Cosman, D. and Pari, L. S. (1989). The murine interleukin-4 receptor: molecular cloning and characterization of secreted and membrane forms. Cell 59:335–348.
29. Marcon, L., Fritz, M. E., Kurman, C. C., Jensen, J. C. and Nelson, D. L. (1988). Soluble TAC peptide is present in the urine of normal individuals and at elevated levels in patients with adult T-cell leukemia. Clin. Exp. Immunol. 73:29–33.
30. Josimovic-Alasevic, O., Hermann, T. and Diamanstein, T. (1988). Demonstration of two distinct forms of released low-affinity type interleukin-2 receptors. Eur. J. Immunol. 18:1855–1857.
31. Goodwin, R. G., Friend, D., Ziegler, S. F., March. C. J., Namen, A. E. and Park, L. S. (1990). Cloning of the human and murine interleukin-7 receptors: demonstration of a soluble form and homology to a new receptor superfamily. Cell 60:941–951.
32. Novick, D., Cohen, B. and Rubinstein, M. (1992). Soluble IFN-a receptor molecules are present in Body Fluids, FEBS Letters, 314:445–448.
33. Pearson, W. R. and Lipman, D. G. (1988), Improved tools for biological sequence comparison, Proc. Natl. Acad. Sci. USA, 85:2444–2448.
34. Okayama, H. and Berg, P. (1983) AcDNA cloning vector that permits expression of cDNA inserts in mammalian cells. Mol. Cell. Biol. 3:280–289.
35. Maniatis et al., Molecular Cloning: A Laboratory Manual, Cold Spring Harbor Laboratory, New York, 1982
36. Gryczan, "The Molecular Biology of the Bacilli", Academic Press, NY (1982), pp. 307–329).
37. Kendall, K. J. et al. (1987) J. Bacteriol. 169:4177–4183).
38. Chater, K F. et al., in "Sixth International Symposium on Actinomycetales Biology", Akademiai Kaido, Budapest, Hungary (1986), pp. 45–54).
39. John, J. F., et al. (1986) Rev. Infect. Dis. 8:693–704).
40. Izaki, K. (1978) Jpn. J. Bacteriol. 33:729–742).
41. Botstein, D., et al. (1982) Miami Wint. Symp. 19:265–274.
42. Broach, J R., in "The Molecular Biology of the Yeast Saccharomyces: Life Cycle and Inheritance", Cold Spring Harbor Laboratory, Cold Spring Harbor, NY, pp. 445–470 (1981).
43. Broach, J. R., (1982) Cell 28:203–204
44. Bollon, D. P., et al. (1980) J. Clin. Hematol. Oncol. 10:39–48.
45. Maniatis, T., in "Cell Biology: A Comprehensive Treatise, Vol. 3: Gene Expression", Academic Press, NY, pp. 563–608 (1980)).
46. Mizushima, S. and Nagata, S. (1990) pEF-BOS, a powerful mammalian expression vector. Nucleic Acid Res. 18:53225328.
47. Byrn R. A. et al., 1990, Nature (London) 344:667–670
48. Frohman, M. A., Dush, M. K. and Martin, G. R. *Proc. Nat'l. Acad. Sci. USA*, 85, 8998–9002.
49. Graham, F. L. and Van der Eb, A. J. (1973) *Virology*, 52, 456–467.
50. Munson, P. J. and Rodbard, D. (1980) *Anal. Biolchem.*, 107, 220–239.
51. Yamada, T. et al., Neurosci. Lett., 181:61–64 (1994).

We claim:

1. An isolated molecule comprising a polypeptide with the sequence of residues 30–237 of SEQ ID NO:2 or residues 30–237 of SEQ ID NO:14; and which molecule binds to one or more of the interferons selected from the group consisting of IFN-α2, IFN-αB, IFN-αC and IFN-β.

2. An isolated molecule which includes a polypeptide with at least 90% identity to the extracellular domain of an IFN-α/β binding protein having the sequence of residues 27–243 of SEQ ID NO:2 or 27–239 of SEQ ID NO:6, which polypeptide retains binding activity to one or more of the interferons selected from the group consisting of IFN-α2, IFN-αB, IFN-αC and IFN-β.

3. An isolated molecule comprising a polypeptide which is a fraction of the extracellular domain of an IFN-α/β binding protein, which extracellular domain consists of the sequence of residues 27–243 of SEQ ID NO:2 or residues 27–243 of SEQ ID NO:14 or residues 27–239 of SEQ ID NO:6, and which fraction retains binding activity to one or more of the interferons selected from the group consisting of IFN-α2, IFN-αB, IFN-αC and IFN-β.

4. An isolated molecule comprising a polypeptide encoded by a DNA molecule which includes nucleotides 313–936 of SEQ ID NO:1 or nucleotides 88–711 of SEQ ID NO:13 or nucleotides 1–717 of SEQ ID NO:5 or encoded by a DNA molecule which is capable of hybridizing to a DNA molecule which includes nucleotides complementary to nucleotides 313–936 of SEQ ID NO:1 or nucleotides complementary to nucleotides 88–711 of SEQ ID NO:13 or nucleotides complementary to nucleotides 1–717 of SEQ ID NO:5 under stringent conditions which are at least as stringent as those at 0.1×SSC and 0.5% SDS at 37° C. for 30–60 minutes, said molecule having binding activity to one or more of the interferons selected from the group consisting of IFN-α2, IFN-αB, IFN-αC and IFN-β.

5. An isolated binding molecule in accordance with claim 1 having the sequence set forth in SEQ ID NO:2.

6. An isolated molecule in accordance with claim 2 having the sequence set forth in SEQ ID NO:6.

7. An isolated molecule in accordance with claim 1 having the sequence set forth in SEQ ID NO:14.

8. A composition comprising a molecule in accordance with claim 1 and a carrier.

9. An isolated antibody which binds specifically to a polypeptide defined in claim 1.

10. An isolated antibody in accordance with claim 9 consisting of a monoclonal antibody.

11. An isolated antibody which binds specifically to a polypeptide defined in claim 2.

12. An isolated antibody in accordance with claim 11 consisting of a monoclonal antibody.

13. An isolated antibody which binds specifically to a polypeptide defined in claim 3.

14. An isolated antibody in accordance with claim 13 consisting of a monoclonal antibody.

15. An isolated antibody which binds specifically to a polypeptide defined in claim 4.

16. An isolated antibody in accordance with claim 15 consisting of a monoclonal antibody.

17. A composition comprising a molecule in accordance with claim 2 and a carrier.

18. A composition comprising a molecule in accordance with claim 3 and a carrier.

19. A composition comprising a molecule in accordance with claim 4 and a carrier.

* * * * *

```
                           SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 1296 base pairs
        (B) TYPE: nucleic acid
        (C) STRANDEDNESS: single
        (D) TOPOLOGY: linear (ii) MOLECULE TYPE: cDNA
```

(ix) FEATURE:
  (A) NAME/KEY: CDS
  (B) LOCATION: 226..1218

(xi) SEQUENCE DESCRIPTION: SEQ ID NO:1:

```
GCTTTTGTCC CCCGCCCGCC GCTTCTGTCC GAGAGGCCGC CCGCGAGGCG CATCCTGACC      60

GCGAGCGTCG GGTCCCAGAG CCGGGCGCGG CTGGGGCCCG AGGCTAGCAT CTCTCGGGAG     120

CCGCAAGGCG AGAGCTGCAA AGTTTAATTA GACACTTCAG AATTTTGATC ACCTAATGTT     180

GATTTCAGAT GTAAAAGTCA AGAGAAGACT CTAAAAATAG CAAAG ATG CTT TTG         234
                                                 Met Leu Leu
                                                   1

AGC CAG AAT GCC TTC ATC GTC AGA TCA CTT AAT TTG GTT CTC ATG GTG       282
Ser Gln Asn Ala Phe Ile Val Arg Ser Leu Asn Leu Val Leu Met Val
      5              10                  15

TAT ATC AGC CTC GTG TTT GGT ATT TCA TAT GAT TCG CCT GAT TAC ACA       330
Tyr Ile Ser Leu Val Phe Gly Ile Ser Tyr Asp Ser Pro Asp Tyr Thr
 20                  25                  30                  35

GAT GAA TCT TGC ACT TTC AAG ATA TCA TTG CGA AAT TTC CGG TCC ATC       378
Asp Glu Ser Cys Thr Phe Lys Ile Ser Leu Arg Asn Phe Arg Ser Ile
                 40                  45                  50

TTA TCA TGG GAA TTA AAA AAC CAC TCC ATT GTA CCA ACT CAC TAT ACA       426
Leu Ser Trp Glu Leu Lys Asn His Ser Ile Val Pro Thr His Tyr Thr
             55                  60                  65

TTG CTG TAT ACA ATC ATG AGT AAA CCA GAA GAT TTG AAG GTG GTT AAG       474
Leu Leu Tyr Thr Ile Met Ser Lys Pro Glu Asp Leu Lys Val Val Lys
         70                  75                  80

AAC TGT GCA AAT ACC ACA AGA TCA TTT TGT GAC CTC ACA GAT GAG TGG       522
Asn Cys Ala Asn Thr Thr Arg Ser Phe Cys Asp Leu Thr Asp Glu Trp
     85                  90                  95

AGA AGC ACA CAC GAG GCC TAT GTC ACC GTC CTA GAA GGA TTC AGC GGG       570
Arg Ser Thr His Glu Ala Tyr Val Thr Val Leu Glu Gly Phe Ser Gly
100                 105                 110                 115

AAC ACA ACG TTG TTC AGT TGC TCA CAC AAT TTC TGG CTG GCC ATA GAC       618
Asn Thr Thr Leu Phe Ser Cys Ser His Asn Phe Trp Leu Ala Ile Asp
                120                 125                 130

ATG TCT TTT GAA CCA CCA GAG TTT GAG ATT GTT GGT TTT ACC AAC CAC       666
Met Ser Phe Glu Pro Pro Glu Phe Glu Ile Val Gly Phe Thr Asn His
            135                 140                 145

ATT AAT GTG ATG GTG AAA TTT CCA TCT ATT GTT GAG GAA GAA TTA CAG       714
Ile Asn Val Met Val Lys Phe Pro Ser Ile Val Glu Glu Glu Leu Gln
        150                 155                 160

TTT GAT TTA TCT CTC GTC ATT GAA GAA CAG TCA GAG GGA ATT GTT AAG       762
Phe Asp Leu Ser Leu Val Ile Glu Glu Gln Ser Glu Gly Ile Val Lys
    165                 170                 175

AAG CAT AAA CCC GAA ATA AAA GGA AAC ATG AGT GGA AAT TTC ACC TAT       810
Lys His Lys Pro Glu Ile Lys Gly Asn Met Ser Gly Asn Phe Thr Tyr
180                 185                 190                 195

ATC ATT GAC AAG TTA ATT CCA AAC ACG AAC TAC TGT GTA TCT GTT TAT       858
Ile Ile Asp Lys Leu Ile Pro Asn Thr Asn Tyr Cys Val Ser Val Tyr
                200                 205                 210

TTA GAG CAC AGT GAT GAG CAA GCA GTA ATA AAG TCT CCC TTA AAA TGC       906
Leu Glu His Ser Asp Glu Gln Ala Val Ile Lys Ser Pro Leu Lys Cys
            215                 220                 225

ACC CTC CTT CCA CCT GGC CAG GAA TCA GAA TCA GCA GAA TCT GCC AAA       954
Thr Leu Leu Pro Pro Gly Gln Glu Ser Glu Ser Ala Glu Ser Ala Lys
        230                 235                 240

ATA GGA GGA ATA ATT ACT GTG TTT TTG ATA GCA TTG GTC TTG ACA AGC      1002
Ile Gly Gly Ile Ile Thr Val Phe Leu Ile Ala Leu Val Leu Thr Ser
    245                 250                 255
```

```
ACC ATA GTG ACA CTG AAA TGG ATT GGT TAT ATA TGC TTA AGA AAT AGC     1050
Thr Ile Val Thr Leu Lys Trp Ile Gly Tyr Ile Cys Leu Arg Asn Ser
260                 265                 270                 275

CTC CCC AAA GTC TTG AGG CAA GGT CTC ACT AAG GGC TGG AAT GCA GTG     1098
Leu Pro Lys Val Leu Arg Gln Gly Leu Thr Lys Gly Trp Asn Ala Val
            280                 285                 290

GCT ATT CAC AGG TGC AGT CAT AAT GCA CTA CAG TCT GAA ACT CCT GAG     1146
Ala Ile His Arg Cys Ser His Asn Ala Leu Gln Ser Glu Thr Pro Glu
                295                 300                 305

CTC AAA CAG TCG TCC TGC CTA AGC TTC CCC AGT AGC TGG GAT TAC AAG     1194
Leu Lys Gln Ser Ser Cys Leu Ser Phe Pro Ser Ser Trp Asp Tyr Lys
        310                 315                 320

CGT GCA TCC CTG TGC CCC AGT GAT TAAGTTTTAT TATGTAGAAA ATAAAGAGCA    1248
Arg Ala Ser Leu Cys Pro Ser Asp
325                 330

AACAGTTACA AAGAAAAAA AAAAAAAAAA AAAAAAAAAA AAAAAAAA                 1296

(2) INFORMATION FOR SEQ ID NO:2:

(i) SEQUENCE CHARACTERISTICS:
        (A) LENGTH: 331 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Leu Ser Gln Asn Ala Phe Ile Val Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240
```

```
Ser Ala Lys Ile Gly Gly Ile Ile Thr Val Phe Leu Ile Ala Leu Val
            245                 250                 255

Leu Thr Ser Thr Ile Val Thr Leu Lys Trp Ile Gly Tyr Ile Cys Leu
            260                 265                 270

Arg Asn Ser Leu Pro Lys Val Leu Arg Gln Gly Leu Thr Lys Gly Trp
            275                 280                 285

Asn Ala Val Ala Ile His Arg Cys Ser His Asn Ala Leu Gln Ser Glu
            290                 295                 300

Thr Pro Glu Leu Lys Gln Ser Ser Cys Leu Ser Phe Pro Ser Ser Trp
305                 310                 315                 320

Asp Tyr Lys Arg Ala Ser Leu Cys Pro Ser Asp
            325                 330

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TACTGGATCC ATGGTNAART TYCCNWSNAT HGT                              33

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TCAAGTCGAC ATNCCYTCNS WYTGYTCYTC DAT                              33

(2) INFORMATION FOR SEQ ID NO:5:

(i) SEQUENCE CHARACTERISTICS:
        (A) LENGTH: 1671 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..717

(xi) SEQUENCE DESCRIPTION: SEQ ID NO:5:

ATG CTT TTG AGC CAG AAT GCC TTC ATC TTC AGA TCA CTT AAT TTG GTT    48
Met Leu Leu Ser Gln Asn Ala Phe Ile Phe Arg Ser Leu Asn Leu Val
  1               5                  10                  15

CTC ATG GTG TAT ATC AGC CTC GTG TTT GGT ATT TCA TAT GAT TCG CCT    96
Leu Met Val Tyr Ile Ser Leu Val Phe Gly Ile Ser Tyr Asp Ser Pro
             20                  25                  30

GAT TAC ACA GAT GAA TCT TGC ACT TTC AAG ATA TCA TTG CGA AAT TTC   144
Asp Tyr Thr Asp Glu Ser Cys Thr Phe Lys Ile Ser Leu Arg Asn Phe
         35                  40                  45

CGG TCC ATC TTA TCA TGG GAA TTA AAA AAC CAC TCC ATT GTA CCA ACT   192
```

```
Arg Ser Ile Leu Ser Trp Glu Leu Lys Asn His Ser Ile Val Pro Thr
 50                  55                  60

CAC TAT ACA TTG CTG TAT ACA ATC ATG AGT AAA CCA GAA GAT TTG AAG         240
His Tyr Thr Leu Leu Tyr Thr Ile Met Ser Lys Pro Glu Asp Leu Lys
 65                  70                  75                  80

GTG GTT AAG AAC TGT GCA AAT ACC ACA AGA TCA TTT TGT GAC CTC ACA         288
Val Val Lys Asn Cys Ala Asn Thr Thr Arg Ser Phe Cys Asp Leu Thr
                 85                  90                  95

GAT GAG TGG AGA AGC ACA CAC GAG GCC TAT GTC ACC GTC CTA GAA GGA         336
Asp Glu Trp Arg Ser Thr His Glu Ala Tyr Val Thr Val Leu Glu Gly
            100                 105                 110

TTC AGC GGG AAC ACA ACG TTG TTC AGT TGC TCA CAC AAT TTC TGG CTG         384
Phe Ser Gly Asn Thr Thr Leu Phe Ser Cys Ser His Asn Phe Trp Leu
        115                 120                 125

GCC ATA GAC ATG TCT TTT GAA CCA CCA GAG TTT GAG ATT GTT GGT TTT         432
Ala Ile Asp Met Ser Phe Glu Pro Pro Glu Phe Glu Ile Val Gly Phe
    130                 135                 140

ACC AAC CAC ATT AAT GTG ATG GTG AAA TTT CCA TCT ATT GTT GAG GAA         480
Thr Asn His Ile Asn Val Met Val Lys Phe Pro Ser Ile Val Glu Glu
145                 150                 155                 160

GAA TTA CAG TTT GAT TTA TCT CTC GTC ATT GAA GAA CAG TCA GAG GGA         528
Glu Leu Gln Phe Asp Leu Ser Leu Val Ile Glu Glu Gln Ser Glu Gly
                165                 170                 175

ATT GTT AAG AAG CAT AAA CCC GAA ATA AAA GGA AAC ATG AGT GGA AAT         576
Ile Val Lys Lys His Lys Pro Glu Ile Lys Gly Asn Met Ser Gly Asn
            180                 185                 190

TTC ACC TAT ATC ATT GAC AAG TTA ATT CCA AAC ACG AAC TAC TGT GTA         624
Phe Thr Tyr Ile Ile Asp Lys Leu Ile Pro Asn Thr Asn Tyr Cys Val
        195                 200                 205

TCT GTT TAT TTA GAG CAC AGT GAT GAG CAA GCA GTA ATA AAG TCT CCC         672
Ser Val Tyr Leu Glu His Ser Asp Glu Gln Ala Val Ile Lys Ser Pro
    210                 215                 220

TTA AAA TGC ACC CTC CTT CCA CCT GGC CAG GAA TCA GAA TTT TCA             717
Leu Lys Cys Thr Leu Leu Pro Pro Gly Gln Glu Ser Glu Phe Ser
225                 230                 235

TAACTTTTTA GCCTGGCCAT TTCCTAACCT GCCACCGTTG AAGCCATGG ATATGGTGGA        777

GGTCATTTAC ATCAACAGAA AGAAGAAAGT GTGGGATTAT AATTATGATG ATGAAAGTGA       837

TAGCGATACT GAGGCAGCGC CCAGGACAAG TGGCGGTGGC TATACCATGC ATGGACTGAC       897

TGTCAGGCCT CTGGGTCAGG CCTCTGTCAT CTCTACAGAA TCCCAGTTGA TAGACCCGGA       957

GTCCGAGGAG GAGCCTGAAC TGCCTGAGGT TGATGTGGAG CTCCCCACGA TGCCAAAGGA      1017

CAGCCCTCAG CAGTTGGAAC TCTTGAGTGG GCCCTGTGAG AGGAGAAAGA GTCCACTCCA      1077

GGACCCTCTT CCCGAAGAGG ACTACAGCTC ACGGGGGGG TCTGGGGCA GAATCACCTT        1137

CAATGTGGAC TTAAACTCTG TGTTTTTGAG AGTTCTTGAT GACGAGGACA GTGACGACTT      1197

AGAAGCCCCT CTGATGCTAT CGTCTCATCT GGAAGAGATG GTTGACCCAG AGGATCCTGA      1257

TAATGTGCAA TCAAACCATT TGCTGGCCAG CGGGGAAGGG ACACAGCCAA CCTTTCCCAG      1317

CCCCTCTTCA GAGGGCCTGT GGTCCGAAGA TGCTCCATCT GATCAAAGTG ACACTTCTGA     1377

GTCAGATGTT GACCTTGGGG ATGGTTATAT AATGAGATGA CTCCAAAACT ATTGAATGAA      1437

CTTGGACAGA CAAGCACCTA CAGGGTTCTT TGTCTCTGCA TCCTAACTTG CTGCCTTATC      1497

GTCTGCAAGT GTTCTCCAAG GGAAGGAGGA GGAAACTGTG GTGTTCCTTT CTTCCAGGTG      1557

ACATCACCTA TGCACATTCC CAGTATGGGG ACCATAGTAT CATTCAGTGG CATTGTTTTA      1617

CAATATTCAA AAGGTGGGCG CCAATTTTGG AAGGGAAGGA ACATGTGCAA CCTT            1671
```

(2) INFORMATION FOR SEQ ID NO:6:

(i) SEQUENCE CHARACTERISTICS:
        (A) LENGTH: 239 amino acids
        (B) TYPE: amino acid
        (D) TOPOLOGY: linear (ii) MOLECULE TYPE: protein (xi) SEQUENCE DESCRIPTION: SEQ ID NO:6:

```
Met Leu Leu Ser Gln Asn Ala Phe Ile Phe Arg Ser Leu Asn Leu Val
 1               5                  10                  15
Leu Met Val Tyr Ile Ser Leu Val Phe Gly Ile Ser Tyr Asp Ser Pro
                20                  25                  30
Asp Tyr Thr Asp Glu Ser Cys Thr Phe Lys Ile Ser Leu Arg Asn Phe
            35                  40                  45
Arg Ser Ile Leu Ser Trp Glu Leu Lys Asn His Ser Ile Val Pro Thr
        50                  55                  60
His Tyr Thr Leu Leu Tyr Thr Ile Met Ser Lys Pro Glu Asp Leu Lys
 65                  70                  75                  80
Val Val Lys Asn Cys Ala Asn Thr Thr Arg Ser Phe Cys Asp Leu Thr
                85                  90                  95
Asp Glu Trp Arg Ser Thr His Glu Ala Tyr Val Thr Val Leu Glu Gly
            100                 105                 110
Phe Ser Gly Asn Thr Thr Leu Phe Ser Cys Ser His Asn Phe Trp Leu
        115                 120                 125
Ala Ile Asp Met Ser Phe Glu Pro Pro Glu Phe Glu Ile Val Gly Phe
    130                 135                 140
Thr Asn His Ile Asn Val Met Val Lys Phe Pro Ser Ile Val Glu Glu
145                 150                 155                 160
Glu Leu Gln Phe Asp Leu Ser Leu Val Ile Glu Glu Gln Ser Glu Gly
                165                 170                 175
Ile Val Lys Lys His Lys Pro Glu Ile Lys Gly Asn Met Ser Gly Asn
            180                 185                 190
Phe Thr Tyr Ile Ile Asp Lys Leu Ile Pro Asn Thr Asn Tyr Cys Val
        195                 200                 205
Ser Val Tyr Leu Glu His Ser Asp Glu Gln Ala Val Ile Lys Ser Pro
    210                 215                 220
Leu Lys Cys Thr Leu Leu Pro Pro Gly Gln Glu Ser Glu Phe Ser
225                 230                 235
```

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATATGTCTAG ATTATATGCT TTTGAGCCAG AATGCCTT                       38

(2) INFORMATION FOR SEQ ID NO:8:

(i) SEQUENCE CHARACTERISTICS:
        (A) LENGTH: 44 base pairs
        (B) TYPE: nucleic acid
        (C) STRANDEDNESS: single (D) TOPOLOGY: linear (ii) MOLECULE TYPE: cDNA (xi) SEQUENCE DESCRIPTION: SEQ ID NO:8:

AATATTCTAG ATAAGCTTAT TAGGCAGATT CTGCTGATTC TGAT                    44

(2) INFORMATION FOR SEQ ID NO:9:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Asp Ser Pro Asp Tyr Thr Asp Glu Ser Arg Thr Phe Lys Ile Arg Leu
1               5                   10                  15

Arg (2) INFORMATION FOR SEQ ID NO:10:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: /note= Xaa = Cys (xi) SEQUENCE DESCRIPTION: SEQ ID NO:10:

Met Ser Lys Pro Glu Asp Leu Lys Val Val Lys Asn Xaa Ala Asn Thr
1               5                   10                  15

Thr Arg (2) INFORMATION FOR SEQ ID NO:11:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (ix) FEATURE:
            (D) OTHER INFORMATION: /note= Xaa = Asn (xi) SEQUENCE DESCRIPTION: SEQ ID NO:11:

Met Ser Gly Xaa Phe Thr Tyr Ile Ile Asp Lys Leu Ile Pro Asn Thr
1               5                   10                  15

Asn Tyr (2) INFORMATION FOR SEQ ID NO:12:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

```
Cys Thr Leu Leu Pro Pro Gly Gln Glu Ser Glu Phe Ser
 1               5                  10
```

(2) INFORMATION FOR SEQ ID NO:13:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

```
ATG CTT TTG AGC CAG AAT GCC TTC ATC TTC AGA TCA CAT AAT TTG GTT     48
Met Leu Leu Ser Gln Asn Ala Phe Ile Phe Arg Ser His Asn Leu Val
 1               5                  10                  15

CTC ATG GTG TAT ATC AGC CTC GTG TTT GGT ATT TCA TAT GAT TCG CCT     96
Leu Met Val Tyr Ile Ser Leu Val Phe Gly Ile Ser Tyr Asp Ser Pro
                20                  25                  30

GAT TAC ACA GAT GAA TCT TGC ACT TTC AAG ATA TCA TTG CGA AAT TTC    144
Asp Tyr Thr Asp Glu Ser Cys Thr Phe Lys Ile Ser Leu Arg Asn Phe
            35                  40                  45

CGG TCC ATC TTA TCA TGG GAA TTA AAA AAC CAC TCC ATT GTA CCA ACT    192
Arg Ser Ile Leu Ser Trp Glu Leu Lys Asn His Ser Ile Val Pro Thr
        50                  55                  60

CAC TAT ACA TTG CTG TAT ACA ATC ATG AGT AAA CCA GAA GAT TTG AAG    240
His Tyr Thr Leu Leu Tyr Thr Ile Met Ser Lys Pro Glu Asp Leu Lys
 65                  70                  75                  80

GTG GTT AAG AAC TGT GCA AAT ACC ACA AGA TCA TTT TGT GAC CTC ACA    288
Val Val Lys Asn Cys Ala Asn Thr Thr Arg Ser Phe Cys Asp Leu Thr
                85                  90                  95

GAT GAG TGG AGA AGC ACA CAC GAG GCC TAT GTC ATC GTC CTA GAA GGA    336
Asp Glu Trp Arg Ser Thr His Glu Ala Tyr Val Ile Val Leu Glu Gly
            100                 105                 110

TTC AGC GGG AAC ACA ACG TTG TTC AGT TGC TCA CAC AAT TTC TGG CTG    384
Phe Ser Gly Asn Thr Thr Leu Phe Ser Cys Ser His Asn Phe Trp Leu
        115                 120                 125

GCC ATA GAC ATG TCT TTT GAA CCA CCA GAG TTT GAG ATT GTT GGT TTT    432
Ala Ile Asp Met Ser Phe Glu Pro Pro Glu Phe Glu Ile Val Gly Phe
    130                 135                 140

ACC AAC CAC ATT AAT GTG ATG GTG AAA TTT CCA TCT ATT GTT GAG GAA    480
Thr Asn His Ile Asn Val Met Val Lys Phe Pro Ser Ile Val Glu Glu
145                 150                 155                 160

GAA TTA CAG TTT GAT TTA TCT CTC GTC ATT GAA GAA CAG TCA GAG GGA    528
Glu Leu Gln Phe Asp Leu Ser Leu Val Ile Glu Glu Gln Ser Glu Gly
                165                 170                 175

ATT GTT AAG AAG CAT AAA CCC GAA ATA AAA GGA AAC ATG AGT GGA AAT    576
Ile Val Lys Lys His Lys Pro Glu Ile Lys Gly Asn Met Ser Gly Asn
            180                 185                 190

TTC ACC TAT ATC ATT GAC AAG TTA ATT CCA AAC ACG AAC TAC TGT GTA    624
Phe Thr Tyr Ile Ile Asp Lys Leu Ile Pro Asn Thr Asn Tyr Cys Val
        195                 200                 205

TCT GTT TAT TTA GAG CAC AGT GAT GAG CAA GCA GTA ATA AAG TCT CCC    672
Ser Val Tyr Leu Glu His Ser Asp Glu Gln Ala Val Ile Lys Ser Pro
    210                 215                 220

TTA AAA TGC ACC CTC CTT CCA CCT GGC CAG GAA TCA GAA TCA GCA GAA    720
Leu Lys Cys Thr Leu Leu Pro Pro Gly Gln Glu Ser Glu Ser Ala Glu
225                 230                 235                 240

TCT GCC AAA ATA GGA GGA ATA ATT ACT GTG TTT TTG ATA GCA TTG GTC    768
```

-continued

```
Ser Ala Lys Ile Gly Gly Ile Ile Thr Val Phe Leu Ile Ala Leu Val
                245                 250                 255

TTG ACA AGC ACC ATA GTG ACA CTG AAA                                795
Leu Thr Ser Thr Ile Val Thr Leu Lys
                260                 265

(2) INFORMATION FOR SEQ ID NO:14:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:14:

Met Leu Leu Ser Gln Asn Ala Phe Ile Phe Arg Ser His Asn Leu Val
 1               5                  10                  15

Leu Met Val Tyr Ile Ser Leu Val Phe Gly Ile Ser Tyr Asp Ser Pro
                20                  25                  30

Asp Tyr Thr Asp Glu Ser Cys Thr Phe Lys Ile Ser Leu Arg Asn Phe
                35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Ile Val Leu Glu Gly
                100                 105                 110

Phe Ser Gly Asn Thr Thr Leu Phe Ser Cys Ser His Asn Phe Trp Leu
                115                 120                 125

Ala Ile Asp Met Ser Phe Glu Pro Pro Glu Phe Glu Ile Val Gly Phe
130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
                180                 185                 190

Phe Thr Tyr Ile Ile Asp Lys Leu Ile Pro Asn Thr Asn Tyr Cys Val
                195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys
                260                 265
```